US012779143B2

(12) United States Patent
Robinson et al.

(10) Patent No.: US 12,779,143 B2
(45) Date of Patent: Nov. 3, 2026

(54) SYSTEMS, DEVICES, AND METHODS FOR ADMINISTERING CANNABINOID MIXTURES

(71) Applicant: Green Sky Creations LLC, Seattle, WA (US)

(72) Inventors: Simon Robinson, Seattle, WA (US); Justin Esterberg, Mesa, AZ (US); Brad Douglass, Black Diamond, WA (US)

( * ) Notice: Subject to any disclaimer, the term of this patent is extended or adjusted under 35 U.S.C. 154(b) by 227 days.

(21) Appl. No.: 18/327,363

(22) Filed: Jun. 1, 2023

(65) Prior Publication Data

US 2024/0131279 A1 Apr. 25, 2024
US 2024/0226463 A9 Jul. 11, 2024

Related U.S. Application Data

(63) Continuation of application No. 17/590,793, filed on Feb. 1, 2022, now Pat. No. 11,701,479.

(51) Int. Cl.
*A61M 11/04* (2006.01)
*A24B 15/167* (2020.01)
(Continued)

(52) U.S. Cl.
CPC ......... *A61M 11/041* (2013.01); *A24B 15/167* (2016.11); *A24F 40/05* (2020.01);
(Continued)

(58) Field of Classification Search
CPC .............. A61M 11/041; A61M 11/005; A61M 2205/502; A61M 15/06; A61M 15/08;
(Continued)

(56) References Cited

U.S. PATENT DOCUMENTS 10,701,969 B2 * 7/2020 Buchberger ............ A24F 42/60
10,994,083 B1 * 5/2021 Habibi .............. A61M 15/0083
(Continued)

FOREIGN PATENT DOCUMENTS

EP 3858161 A1 * 8/2021 ............ A24F 40/10
KR 20210072525 A * 6/2021
(Continued)

OTHER PUBLICATIONS

English translation for KR 20210072525, machined translated by espacenet.com.*
(Continued)

*Primary Examiner* — Tu A Vo

(57) ABSTRACT

A nebulizer device for administering aerosol cannabinoid mixtures to a user includes a mouthpiece, a first reservoir, a second reservoir, and a nebulizer device. The nebulizer module is configured to receive a first dosage of the first liquid from the first reservoir and a second dosage of a second liquid from the second reservoir. The nebulizer module is also configured to transform the first liquid into an inhalant and the second liquid into an aerosol that are provided to the user through the mouthpiece. The device further includes a dosage module configured to independently control the delivery of the first liquid and the second liquid to the nebulizer module to set a ratio between the first dosage of the first liquid and the second dosage of the second liquid. The dosage module thereby controls a composition of an aerosol cannabinoid mixture administered to the user.

13 Claims, 9 Drawing Sheets

(51) Int. Cl.

| | |
|---|---|
| ***A24F 40/05*** | (2020.01) |
| ***A24F 40/10*** | (2020.01) |
| ***A24F 40/30*** | (2020.01) |
| ***A24F 40/42*** | (2020.01) |
| ***A24F 40/46*** | (2020.01) |
| ***A24F 40/48*** | (2020.01) |
| ***A24F 40/50*** | (2020.01) |
| ***A24F 40/65*** | (2020.01) |
| ***A61K 9/00*** | (2006.01) |
| ***A61M 11/00*** | (2006.01) |
| ***A61M 15/00*** | (2006.01) |
| ***A61M 15/06*** | (2006.01) |
| ***A61M 15/08*** | (2006.01) |

(52) U.S. Cl.

CPC .............. *A24F 40/10* (2020.01); *A24F 40/30* (2020.01); *A24F 40/42* (2020.01); *A24F 40/46* (2020.01); *A24F 40/48* (2020.01); *A24F 40/50* (2020.01); *A24F 40/65* (2020.01); *A61K 9/0078* (2013.01); *A61M 11/005* (2013.01); *A61M 15/0021* (2014.02); *A61M 15/0085* (2013.01); *A61M 15/06* (2013.01); *A61M 15/08* (2013.01); *A61M 2205/502* (2013.01)

(58) Field of Classification Search

CPC .......... A61M 15/0085; A61M 15/0003; A61M 15/001; A61M 15/0021; A24B 15/167; A24F 40/65; A24F 40/48; A24F 40/10; A24F 40/46; A24F 40/05; A24F 40/30; A24F 40/42; A24F 40/50; A61K 9/0078; A61K 36/185

See application file for complete search history.

(56) References Cited

U.S. PATENT DOCUMENTS

| | | | | |
|---|---|---|---|---|
| 11,219,725 | B1 * | 1/2022 | Habibi | A61M 15/0021 |
| 11,701,479 | B1 * | 7/2023 | Robinson | A24B 15/167 128/200.16 |
| 2007/0074722 | A1 * | 4/2007 | Giroux | A61M 11/06 128/203.15 |
| 2010/0163041 | A1 * | 7/2010 | Hyde | G16H 20/13 340/618 |
| 2014/0123989 | A1 * | 5/2014 | LaMothe | A61M 15/0003 131/328 |
| 2014/0243749 | A1 * | 8/2014 | Edwards | H04B 1/3827 455/73 |
| 2016/0089508 | A1 * | 3/2016 | Smith | A61M 15/0085 128/202.21 |
| 2017/0262613 | A1 * | 9/2017 | Ljungberg | A61M 15/0083 |
| 2017/0266397 | A1 * | 9/2017 | Mayle | A61M 15/06 |
| 2017/0295843 | A1 * | 10/2017 | Storch | A61M 11/041 |
| 2017/0303591 | A1 * | 10/2017 | Cameron | H05B 1/0244 |
| 2018/0049477 | A1 * | 2/2018 | Suzuki | A61M 15/06 |
| 2018/0110941 | A1 * | 4/2018 | Smith | A61M 15/0066 |
| 2018/0289062 | A1 * | 10/2018 | Lopez | A61K 31/00 |
| 2018/0318529 | A1 * | 11/2018 | Davidson | A61M 15/0051 |
| 2019/0343182 | A1 * | 11/2019 | Yilmaz | H05B 3/44 |
| 2020/0061301 | A1 * | 2/2020 | Hatamian | A61M 5/31546 |
| 2020/0061314 | A1 * | 2/2020 | Hatamian | A61M 15/0083 |
| 2020/0107578 | A1 * | 4/2020 | Rubin | A24B 15/167 |
| 2020/0352249 | A1 * | 11/2020 | Achtien | A61M 15/0066 |
| 2020/0353187 | A1 * | 11/2020 | Pell | A61L 2/24 |
| 2021/0023315 | A1 * | 1/2021 | Goldenberg | A61M 15/0025 |
| 2021/0346616 | A1 * | 11/2021 | Krietzman | A61M 15/08 |
| 2021/0366589 | A1 * | 11/2021 | Hatamian | G07C 9/00563 |
| 2021/0402110 | A1 * | 12/2021 | Pauley | G16H 40/67 |
| 2022/0022537 | A1 * | 1/2022 | Murray | A24F 40/485 |
| 2022/0280732 | A1 * | 9/2022 | Jiang | G01N 15/0205 |
| 2023/0354891 | A1 * | 11/2023 | Batista | A24F 40/485 |

FOREIGN PATENT DOCUMENTS

| | | | | | |
|---|---|---|---|---|---|
| WO | WO-2019122880 | A1 * | 6/2019 | A24F 40/30 |
| WO | WO-2020165777 | A1 * | 8/2020 | |
| WO | WO-2021202937 | A1 * | 10/2021 | A24F 40/05 |
| WO | WO-2023044998 | A1 * | 3/2023 | A61M 11/042 |

OTHER PUBLICATIONS

English translation for WO 2023/044998, machine translated by espacenet.com.*

* cited by examiner

300 Screenshot

104 Database

| User: Sam | Days | Composition | | Flavor profile | | Temperature | |
|---|---|---|---|---|---|---|---|
| | | CBD | Flavor Compound | Form of Flavor Compound | Volume (mL) | Cannabinoid | Flavor Compound |
| Profile 1 | 12/18/2020 | 1 | 4 | Vapor liquid | 1 | 370°F | 320°F |
| Profile 2 | 12/19/2020 | 2 | 3 | Vapor liquid | 2 | 400-430°F | 320°F |
| Profile 3 | 12/20/2020 | 3 | 2 | Filter | 3 | 315°F | N/A |
| Profile 4 | 12/21/2020 | 4 | 1 | mouthpiece | 4 | 370°F | N/A |
| Profile 5 | 12/22/2020 | 2 | 4 | mouthpiece | 1 | 400-430°F | N/A |
| Profile 6 | 12/23/2020 | 3 | 3 | Filter | 2 | 315°F | N/A |
| Profile 7 | 12/24/2020 | 4 | 4 | Vapor liquid | 1 | 370°F | 320°F |

*FIG. 3*

SYSTEMS, DEVICES, AND METHODS FOR ADMINISTERING CANNABINOID MIXTURES

CROSS-REFERENCE TO RELATED APPLICATION

This application is a continuation of U.S. patent application Ser. No. 17/590,793, filed Feb. 1, 2022, which is incorporated herein by reference in its entirety.

FIELD OF THE DISCLOSURE

The present disclosure is generally related to devices, systems, and methods for controlling vaporizing and/or aerosolizing cannabinoids and other substances. More specifically, the present disclosure is directed toward vaporizing and/or aerosolizing materials from a plurality of reservoirs and either combining, or maintaining separation between, the vaporizable materials to achieve precise dosing, flavor control, and/or decreased health risk to the user.

BACKGROUND

Cannabinoids are commonly consumed using vaporization or aerosolization devices that utilize a liquid cannabinoid extract, which is then converted into a vapor- and aerosol-containing output stream that the user can inhale. Vaporization refers to an instance where a solid, semi-solid or liquid changes physical state into a gas. Aerosolization refers to the process or act of converting a physical substance or substances into the form of particles small and light enough to be carried on the air. Output stream refers to the combination of vapor and aerosol that results from quickly heating heterogenous substances in the presence of a directional carrier gas. Some cannabinoids, such as tetrahydrocannabinolic acid (THCA), require a significant amount of heat to drive the chemical decarboxylation process which produces neutral or decarboxylated cannabinoids, such as tetrahydrocannabinol (THC). THC possesses psychoactive effects, but THCA does not. Decarboxylation is often referred to as an "activation" step for cannabinoids. When using non-acidic and already "activated" cannabinoids, such as THC, a significant amount of heat is still required to incorporate it into an output stream since non-acidic cannabinoids possess boiling points at atmospheric pressure above 350° F. (ca. 175° C.).

Research indicates that users of various age groups often prefer flavored vapor products to unflavored vapor products. However, heating flavor compounds to elevated temperatures at which co-mingled, higher molecular weight compounds, such as cannabinoids, will vaporize, aerosolize, and/or, optionally, decarboxylate, may cause the flavor compounds to undergo combustion or to thermally degrade into other, potentially hazardous compounds or compounds with diminished organoleptic properties.

Vaporizers utilizing a single reservoir containing both cannabinoids and flavor compounds can result in a first inhalation draw composed of more flavor compounds than cannabinoids despite there being significantly more cannabinoids in the liquid formulation in the reservoir. This is the result of flavor compounds typically possessing much lower boiling points than cannabinoids leading to increased volatility of the flavor compounds relative to cannabinoids. Some flavor compounds are sufficiently volatile that they do not require any additional heat to instigate aerosolization or to incorporate into an output stream to stimulate olfactory and gustatory sensations. Such a discrepancy in volatility can drive the imbalance of flavor compounds versus cannabinoids in the output stream, especially in heating regimes where the temperature is non-optimized (e.g., while the heating element of the device is heating up).

The thermal-degradation products (i.e., byproducts) of vapor product additives may cause lung irritation or other hazards to lung tissue or the corporeal user. For example, vitamin E acetate [CAS #: 7695-91-2] has been used as an additive in illicit cannabis vapor products resulting in acute lung conditions that have been termed e-cigarette and vape-associated lung illness (EVALI). Although the root-cause or -causes of EVALI are not yet definitive, it appears that vitamin E acetate can decompose into acidic solvents, such as acetic acid, with temperatures above 200° C. and may even decompose into the highly reactive and lung-tissue damaging compound ketene at temperatures above 350° C. In addition, flavor compounds themselves can degrade into problematic residual solvents (e.g., terpinolene→acetone) and other compounds in the presence of heat and oxygen via dehydrogenation, epoxidation, double-bond cleavages, allylic oxidation, and rearrangement reactions. These byproducts of the heating and output stream generation process can potentially occur even when the intended additive is relatively benign. There exists a need to create a device which decouples the higher boiling point substances (e.g., cannabinoids) from the lower boiling point substances (e.g., flavor) in the process of vaporization and/or aerosolization, thus creating an output stream or streams.

Therefore, there is a need in the field for improved devices, systems, and methods for providing cannabinoid mixtures to the users.

DESCRIPTIONS OF THE DRAWINGS

FIG. 3 shows a screenshot of a display displaying a device database, in accordance with some embodiments.

DETAILED DESCRIPTION

Figure 1:
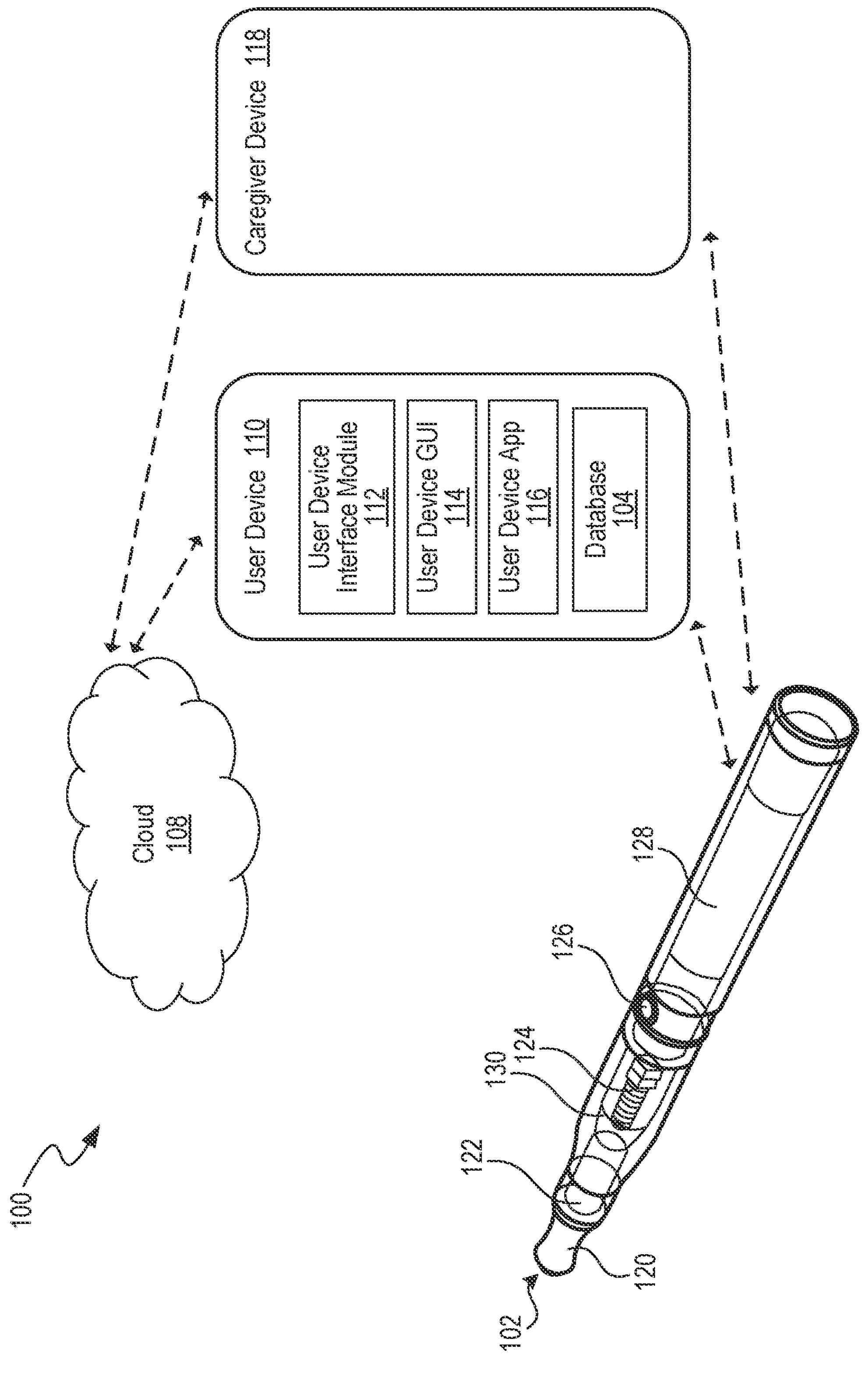
FIG. 1 illustrates a system for producing and providing a decoupled cannabinoid vapor and flavor vapor, in accordance with some embodiments.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The devices, systems, and methods of the present disclosure provide for improved experiences of inhalable cannabinoid compounds by providing safe and convenient means for inhaling cannabinoid and flavor compounds in desired combinations. The present disclosure allows a user to inhale an aerosol cannabinoid mixture including a vaporized cannabinoid compound and an aerosolized flavor compound simultaneously. Dosages of the respective compounds in the mixture aerosol cannabinoid may be automatically adjusted based on the user's preferences. In some implementations, the respective dosages are adjusted over time while the user is inhaling the aerosol cannabinoid mixture. For example, the dosages may be adjusted based on the user's preferences, biometric indications, or other parameters (e.g., time of day). This provides an automated and convenient way for the user to enjoy inhaling the user-specific aerosol cannabinoid mixture.

In accordance with some embodiments, a portable nebulizer device is configured for administering aerosol cannabinoid mixtures to a user. The nebulizer device includes a mouthpiece, a first reservoir and a second reservoir, a nebulizer module, and a dosage module. The nebulizer module is fluidically coupled to the first reservoir and the second reservoir. The first reservoir includes a first liquid and the second reservoir includes a second liquid. The nebulizer module is configured to receive a first dosage of the first liquid and a second dosage of the second liquid. The nebulizer module transforms the first liquid into an inhalant (e.g., a vapor) and the second liquid into an aerosol. The dosage module is configured to independently control the delivery of the first liquid and the second liquid. In particular, the dosage module is configured to set a ratio between the first dosage and the second dosage to control a composition of an aerosol cannabinoid mixture administered to the user through the mouthpiece. The aerosol cannabinoid mixture includes the inhalant and the aerosol.

In accordance with some embodiments, a portable nebulizer device is configured for administering psychoactive mixtures to a user. The nebulizer device includes a first reservoir and a second reservoir, a nebulizer module, and a dosage module. The nebulizer module is fluidically coupled to the first reservoir and the second reservoir. The first reservoir includes a first liquid and the second reservoir includes a second liquid. The nebulizer module is configured to receive a first dosage of the first liquid and a second dosage of the second liquid. The nebulizer module transforms the first liquid into an inhalant (e.g., a vapor) and the second liquid into an aerosol. The aerosol psychoactive mixture includes the inhalant and the aerosol.

In accordance with some embodiments, a method for administering aerosol compounds to a user with a nebulizer device is disclosed. The nebulizer device includes an inhalation interface, a first reservoir, a second reservoir, a nebulizer module, and a dosage module. The nebulizer module is coupled with the first reservoir and the second reservoir. The method includes receiving with the nebulizer device a first dosage of a first liquid from the first reservoir and a second dosage of a second liquid from the second reservoir. The method includes transforming, with the nebulizer module, the received first liquid into an inhalant and the received second liquid into an aerosol that is provided to the user. The method includes controlling independently, with the dosage module, delivery of the first liquid and the second liquid to the nebulizer module to set a ratio between the first dosage of the first liquid and the second dosage of the second liquid. The dosage module thereby controls a composition of an aerosol cannabinoid mixture administered through the inhalation interface to the user.

In accordance with some embodiments, a controller module for controlling administering of aerosol cannabinoid mixtures to a user by a portable nebulizer device is disclosed. The controller module includes a processor and a memory storing instructions which, when executed by the processor, cause the nebulizer device to perform processes. The processes include receiving, with a nebulizer module coupled with a first reservoir and a second reservoir distinct from the first reservoir, a first dosage of a first liquid from the first reservoir and a second dosage of a second liquid from the second reservoir. The processes include transforming, with the nebulizer module, the received first liquid into an inhalant and the received second liquid into an aerosol that are provided to the user. The processes also include controlling independently, with the dosage module, delivery of the first liquid and the second liquid to the nebulizer module to set a ratio between the first dosage of the first liquid and the second dosage of the second liquid. The dosage module thereby controls a composition of an aerosol cannabinoid mixture administered through a mouthpiece to the user. The aerosol cannabinoid mixture includes the inhalant and the aerosol. The nebulizer device can include one or more sensors used to monitor the aerosol cannabinoid mixture. The controller module can control operation of the nebulizer device to keep the aerosol cannabinoid mixture within an acceptable range (e.g., a range set by the user, caregiver, healthcare provider, etc.).

In accordance with some embodiments, a system for providing aerosol compounds to a user is disclosed. The system includes a nebulizer and a user device in communication with the nebulizer device. The nebulizer device includes a mouthpiece, a first reservoir, a second reservoir, and a dosage module. The nebulizer module is fluidically coupled to the first reservoir and the second reservoir. The nebulizer module is configured to receive a first dosage of a first liquid from the first reservoir and a second dosage of a second liquid from the second reservoir. The nebulizer module is further configured to transfer the first liquid into an inhalant and second liquid into an aerosol that are provided to the user. The dosage module is configured to independently control delivery of the first liquid and the second liquid to the nebulizer module to set a ratio between the first dosage of the first liquid and the second dosage of the second liquid. The dosage module thereby controls a composition of an aerosol cannabinoid mixture administered to the user through the mouthpiece. The aerosol cannabinoid mixture includes the inhalant and the aerosol. The user device includes a processor and a memory storing instructions which, when executed by the processor, cause the user device to perform processes. The processes include receiving a dosing schema from the user of the user device. The dosing schema includes the ratio between the first dosage of the first liquid and the second dosage of the second liquid. The dosing schema is associated with the user of the nebulizer device. The processes also include providing instructions to the nebulizer device to administer the first dosage of the first liquid and the second dosage of the second liquid to the nebulizer module in accordance with the dosing schema.

In some embodiments, a system for stimulating the perception of flavor in a vapor or aerosol device (e.g., a nebulizer device) is disclosed. The perception of flavor in an inhalant or aerosol is stimulated without the presence of flavor compounds in an inhalant liquid or oil containing at least one active ingredient. The flavor composition may be combined into one inhalant stream with the active ingredients prior to inhalation by a user. The flavor composition may be a liquid stored in a physically separate reservoir than that containing the at least one active ingredient.

In some embodiments, the physically separate flavor composition is acted upon by a controllable aerosolization element independent from an element that acts upon the at least one active ingredient. The heat or temperature of the elements may be separately controlled. The aerosol stream from the first reservoir may pass through the reservoir containing the at least one active ingredient or not pass through the reservoir containing the at least one active ingredient.

In some embodiments, the flavor composition is coated upon or impregnated within the mouthpiece of the aerosol device. The flavor composition can be coated upon or impregnated within the reservoir containing the at least one active ingredient.

In some embodiments, the device minimizes the risk of flavor compounds thermally degrading into harmful compounds. The system may protect a thermally or oxidatively unstable flavor composition from degrading into other compounds with undesirable organoleptic properties. The system may aerosolize the inhalant liquid, the oil containing at least one active ingredient, or both using a method of nebulization that does not increase the temperature of the liquid or liquids beyond a temperature limit, such as 50 degrees Celsius in the process of creating an aerosol. In some embodiments, the system includes a nebulizer that is used to aerosolize the flavor composition.

In some embodiments, the system is configured to deliver both of the liquids intranasally. In such embodiments, the flavor composition is not combined into one inhalant stream with the active ingredients prior to inhalation by a user. The flavor composition may be aerosolized and introduced directly to the nasal passages of the user or introduced into the atmosphere around the user. In some embodiments, the disclosed system impacts the perception of flavor using virtual reality, non-chemical stimulation of taste receptors, or direct brain stimulation of cortical brain areas. In some embodiments, a system for stimulating the perception of aroma in a vapor or aerosol device is disclosed, and the stimulation is done without the presence of aroma compounds in an inhalant liquid or oil containing at least one active ingredient. In some embodiments, the system impacts. the perception of aroma using virtual reality, non-chemical stimulation of aroma receptors, or direct brain stimulation of cortical brain areas. In some embodiments, the at least one active ingredient is related to or derived from cannabis and/or tobacco.

In some embodiments, a device can independently deliver cannabinoid substances and other substances. The device can control the number of substances, dosage, ratio of substances, temperature, and/or characteristics of the administered substances. For example, the device can combine a cannabinoid inhalant (e.g., cannabinoid vapor, gas, etc.) and one or more flavor inhalants. For example, the device can vaporize flavor compounds independent of administering the cannabinoids to reduce the risk to the user.

In some embodiments, a device can decouple vaporization of flavor compounds from vaporization of cannabinoids to reduce the risk to the user. In addition, separating the exposure routes and conditions of flavor compounds from cannabinoids may enable the safe and compliant use of flavor compounds even in regulatory environments which could restrict product manufacturers from the direct flavoring of vapor products that contain cannabinoids and/or other substances.

Systems and Devices

FIG. 1 illustrates a system 100 for producing and providing decoupled inhalants, in accordance with some embodiments. The system 100 includes a nebulizer device 102, a user device 110, and an optional caregiver device 118. The nebulizer device 102, the user device 110, and the optional caregiver device 118 are in communication with each other. In some embodiments, the devices are in a wireless communication with each other (e.g., via Bluetooth or other short-range wireless communication protocols). In some embodiments, the system 100 further includes a cloud 108 (e.g., a network hosted by a public or private cloud platform that is available on demand) for facilitating operations of system 100.

The nebulizer device 102 can be configured to provide inhaled mixtures (e.g., aerosolized mixtures of cannabinoid compounds and flavor compounds) and can include one or more mouthpieces 120, reservoirs 122, a nebulizer module 124, and a dosage module 130, as shown in FIG. 1. The mouthpiece 120 is an element that a user of the nebulizer device uses to inhale mixtures (e.g., vapors and/or aerosols), including flavor and active compounds. The reservoirs 122 are configured to store the flavor and/or active ingredient compounds prior to nebulization (e.g., evaporation or atomization). In some embodiments, the reservoirs 122 include two or more reservoirs for storing two or more compounds. For example, the reservoirs 122 include a first reservoir for storing one or more cannabinoid compounds and a second reservoir for storing one or more flavor compounds. In some embodiments, the reservoirs 122 include a plurality of first reservoirs each storing one or more cannabinoid compounds (e.g., tetrahydrocannabinol compounds, cannabidiol compounds, single or multiple strains, etc.) and a plurality of second reservoirs each storing one or more flavor compounds. The nebulizer device 102 can selectively combine the compounds to produce a desired mixture, including, for example, vapor mixtures, aerosol mixtures, vapor/aerosol mixtures (e.g., a mixture of one or more aerosolized flavor compounds (e.g., vape juice, vapor flavoring, etc.) and one or more vaporized cannabinoid compounds, a mixture of one or more cannabinoids, etc. In some embodiments, the cannabinoid compound includes one or more cannabinoids (e.g., THC, cannabidiol (CBD), cannabinol (CBN), and/or any other cannabinoid). The cannabinoids can be infused in a carrier oil such as coconut oil, hemp seed oil, or other matrix acceptable for intraoral, intranasal, respiratory or environmental delivery. In some embodiments, the flavor compounds and formulations can be introduced in substantially pure form without the need for a carrier or any excipients since they are typically liquids. In some embodiments, the ratio of flavor compounds to cannabinoid compounds is reproducibly between 1:10 and 1:5 to achieve a concentration of flavor compounds in the output stream that is enjoyable for the user. In some embodiments, the ratio of flavor compounds to cannabinoid compounds is reproducibly greater than 1:5 and is still enjoyable thus overcoming a typical limit of heated vaporization devices where the elevated temperature and/or degradation of the flavor compounds lead to an overly "harsh" sensation to the user. In some embodiments, the ratio of flavor compounds to cannabinoid compounds is reproducibly between 1:100 and 1:25 via direct introduction of the flavor compounds to the nasal passages or into the immediate environment around the nose such that the efficiency of the flavor signal on flavor perception is stronger via this olfactory targeting. In some embodiments, the ratio of flavor compounds to cannabinoids is less than 1:100 that still leads to conscious flavor perception from the user due to precise olfactory targeting. In some other embodiments, the ratio of flavor compounds to cannabinoids is less than 1:100 leading to a sub-conscious or subliminal perception of flavor and/or aroma.

The nebulizer module 124 can include a nebulizing element capable of transforming a liquid into an aerosol or a mist. Alternatively, the nebulizer module 124 can include a heater (e.g., a resistive heater, Peltier device, etc.) capable of transforming a liquid into a vapor. The liquid may include a liquid including one or more flavor compounds and/or a liquid including one or more active ingredients (e.g., cannabinoids, psychoactive substances, etc.) received from the reservoirs 122. The dosage module 130 includes one or more elements (e.g., valves, dials, buttons, etc.) for controlling the flow of the liquids from the reservoirs 122 to the nebulizer module 124. Controlling the flow can include turning the liquid flows on and off, as well as controlling the flow rates. In some embodiments, the nebulizer device 102 further includes one or more control buttons (e.g., a button 126 such as a power button) and one or more power sources (e.g., a battery 128). The button 126 allows the user to supply the nebulizer module 124 with power from the battery 128 in order to nebulize the liquids stored in the reservoirs 122. In some embodiments, the battery 128 is a lithium-ion battery. The nebulizer device 102 is portable. The nebulizer device 102 may have a size comparable to a pen. Different embodiments of the nebulizing device are described in further detail with respect to FIGS. 2A-2C.

Figure 6:
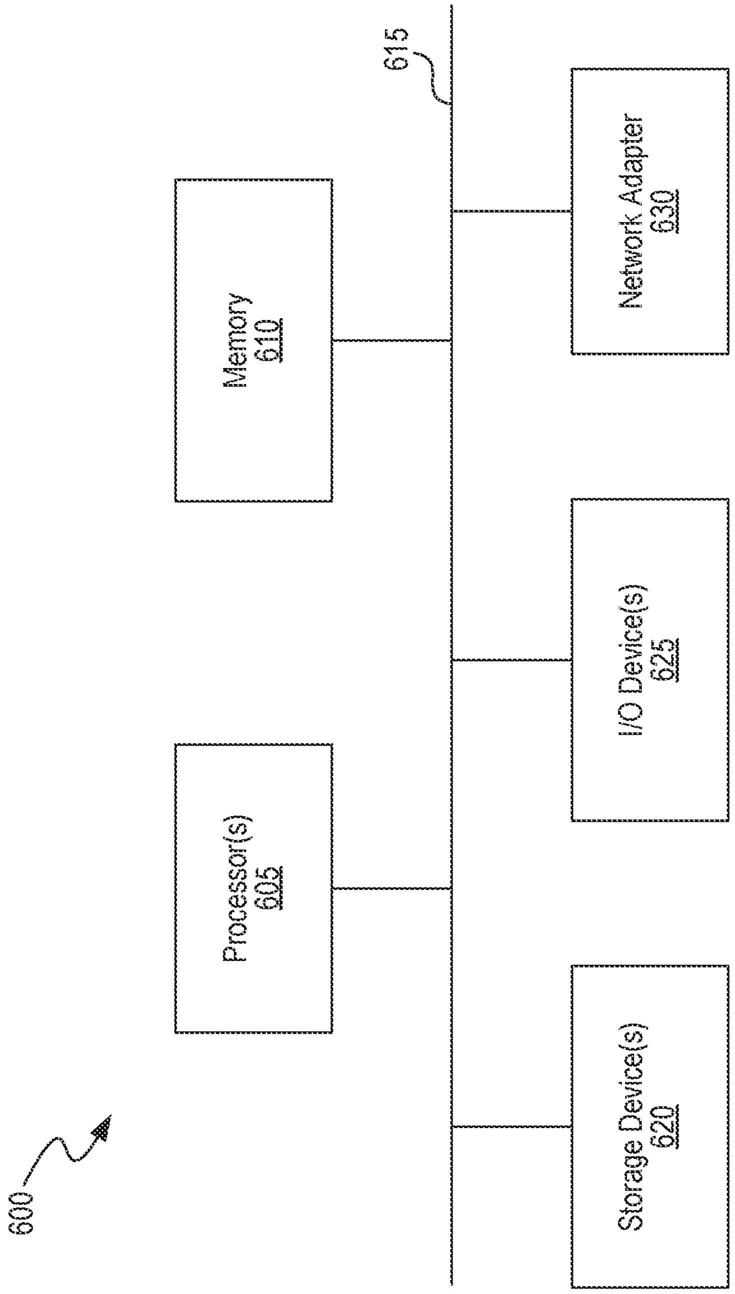
FIG. 6 is a block diagram of a computer system as may be used to implement features of some embodiments of the disclosed technology.

The user devices 110 may be a computing device, laptop, smartphone, tablet, computer, smart speaker, or I/O device (e.g., a computing device described with respect to FIG. 6). In some embodiments, the user device 110, nebulizer device 102, and/or caregiver device 118 of system 100 communicate with each other via the cloud 108 or other communication network (e.g., a local area network (LAN), a wide area network (WAN), etc.). The communication may be via a wired and/or a wireless network. The communication network, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), radio waves, and other communication techniques known in the art. The communication network may allow ubiquitous access to shared pools of configurable system resources and higher-level services that can be rapidly provisioned with minimal management effort, often over the Internet and relying upon shared resources to achieve coherence and economies of scale, like a public utility, while third-party clouds enable organizations to focus on their core businesses instead of expending resources on computer infrastructure and maintenance, shown as cloud 108.

In some embodiments, the system 100 further includes the caregiver device 118. The caregiver device 118 may correspond to a computing device (e.g., the computing device as described with respect to FIG. 6). The caregiver device 118 may be in communication with the nebulizer device 102 and/or the user device 110 via a wired or wireless communication (e.g., via Bluetooth, WiFi, or the cloud 108). In some embodiments, the caregiver device 118 can be configured to allow a caregiver (e.g., a physician, a therapist, or other healthcare worker or entity) to interact with the user. In some embodiments, the caregiver can use the caregiver device 118 to set the dosage to be given to the user by providing instructions to the nebulizer device 102 or to the user device 110. For example, the caregiver device 118 accesses the database 104 of the user device 110 to set values of the dosage scheme.

The system 100 allows a user to control the proportions of the cannabinoid and flavor compounds that the user wants to inhale from the nebulizer device 102 via the user device 110. The proportions can be varied or constant over dosing, a period of time, etc. In particular, the user may control the proportions of cannabinoid and flavor compounds via a user device app 116 on the user device 110. In some embodiments, the system includes a database associated with the user device 110 and/or nebulizer device 102. In some embodiments, database 104 is included in the user device 110 (e.g., database 104 in FIG. 1) or the nebulizer device 102. In some embodiments, the database is associated with the cloud 108 and is accessible by the user device 110 (e.g., the cloud-based database may be accessed via the user device app 116). Database 104 of the user device 110 may include a dosage scheme (e.g., a compound profile) including forms and relative volumes, mass, or weights of the flavor and cannabinoid compounds to be provided to the user. The dosage scheme may be provided or determined by a user (e.g., via a user input on the user device 110). The database 104 can also include ingredient information, thermal processing scheme, etc. Alternatively and additionally, the dosage scheme may also be predetermined (e.g., based on the user's profile or the type of compounds that are stored in the reservoirs 122).

In some embodiments, the dosage scheme determines relative volumes or weights of the cannabinoid compound and the flavor compound to be inhaled by the user. For example, a ratio of a volume or mass of the cannabinoid compound with respect to a volume or mass of the flavor compound is 100:1, 50:1, 25:1; 20:1; 15:1; 10:1; 5:1; 5:2; 1:1; or 2:1. The dosage volume of the cannabinoid compound(s) and the flavor compound(s) minus any amount of diluent or matrix can range from 0.1 μL to 0.01 mL, from 0.2 μL to 0.05 mL, from 0.5 μL to 0.1 mL, from 1 μL to 0.08 mL, from 1 μL to 0.05 mL, from 1 μL to 04 mL, or from 1 μL to 03 mL. In some embodiments, a volume of the cannabinoid compound(s), the flavor compound(s), and liquid diluent or matrix compounds to be aerosolized or nebulized range from 0.1 μL to 5 mL, from 0.1 μL to 10 mL, from 0.1 μL to 8 mL, from 0.1 μL to 5 mL, from 0.1 μL to 4 mL, or from 0.1 μL to 3 mL dependent upon the concentration of the cannabinoid(s) and flavor compound(s) in the diluent or matrix material. In some embodiments, a total volume of the output stream (e.g., a single inhalation, a dose, etc.) containing cannabinoid compound(s), the flavor compound(s), liquid diluent or matrix compounds, and carrier air or gas ranges from 1.0 mL to 10 mL, from 2.0 mL to 50 mL, from 5.0 mL to 100 mL, from 1.0 mL to 80 mL, from 10 mL to 500 mL, from 10 mL to 1.0 L, or from 100 mL to 10 L dependent on the concentration of cannabinoid(s) and flavor compound(s) in the matrix, the ratio of the flavored cannabinoid matrix to the output stream gas, the duration of the user session, and the style of aerosolization or nebulization device (e.g. pulsed or steady flow, continuous user inhalation or intermittent inhalation and environmental release). In some embodiments, low flow rates are utilized, such as in the milliliter per minute range. In some embodiments, high flow rates are utilized, such as in the liter per minute range. And in some embodiments both high and low flow rates are utilized for example with parallel output streams of different compositions or during pulsed flow regimes where a high concentration of cannabinoid compound(s) and/or flavor compound (s) to carrier gas is first required during one time period followed by a low concentration regime in a second time period.

For example, the device database 104 includes profiles for a user based on the desired composition of cannabinoid and flavor compound for one week along with the flavor profile. In some embodiments, the ratio of cannabinoids to flavors may also depend on the concentration of cannabinoids and flavors in respective compositions. In some embodiments, the ratio may be based, at least in part, on the potency of the compositions. In some embodiments, the database 104 may comprise a plurality of profiles corresponding to a user. The profiles may comprise information such as days, composition, and flavor profile corresponding to the user. For example, the database 104 may include profile 1 corresponding to date 12/18/2020 when the user consumed compositions of CBD to flavor in a 1:4 ratio and a flavor profile with vapor-liquid of 1 mL, as illustrated in a screenshot of the device database 104 in FIG. 3.

The user device 110 may send the information related to the dosage scheme to the nebulizer device 102. For example, the user device 110 sends the information related to the dosage scheme to a controller of the nebulizer device 102 (e.g., a control system or controller 132 in FIG. 2A including a receiver, a processor, and a memory for controlling operations of the nebulizer device). Based on the received dosage scheme, the dosage module 130 may provide dosages of respective liquids from the reservoirs 122 to the nebulizer module 124 by controlling the volume and/or flow of the liquids. The nebulizer device 102 may communicate with other components and systems of the system 100. For example, the nebulizer device 102 can wirelessly receive dosing schemes, settings, control programs, calibration routines, etc. and can send information (e.g., or data (e.g., sensor readings, substance data, etc.)

In some embodiments, the user device 110 includes a user device interface module 112 that may utilize the user device graphic user interface (GUI) 114 to facilitate the user to input data. The user device interface module 112 may be triggered when the user signs in to the user device app 116 on the user device 110. In some embodiments, the user device interface module 112 may receive the dosage scheme from the user via the user device interface module 112. The user device interface module 112 may display information on the user device GUI 114. For example, the user device interface module 112 may display information such as the scheme (e.g., dosage scheme, thermal processing scheme, etc.), user profile, compound information (e.g., number and composition of cannabinoid and flavor compounds), recommended protocols, safety information, etc., on the user device GUI 114 (e.g., as illustrated in FIG. 3). In some embodiments, user device interface module 112 may display the total dose provided to the user, the maximum dose for a particular day or period of time, and/or the dose regimen over previous days or periods of time. In some embodiments, the user device interface module 112 may facilitate the user to track the dose of cannabinoid and the flavor compound. In some embodiments, the user device interface module 112 facilitates the user to enter subjective measures that relate to dosing, pain levels, intoxication levels, etc. In some embodiments, the user device interface module 112 facilitates the user to request a caregiver (e.g., the caregiver device 118) to modify the daily dose (i.e., increase or decrease the total cannabinoids allowed) based on the subjective information (such as too much pain, too much intoxication, etc.).

In some embodiments, the user device 110 automatically controls dosing based on, for example, a schedule, user feedback, biometrics (e.g., biometrics from one or more wearables), caregiver, etc. For example, the controller 132 can be programmed to automatically adjust the dosing based on the time of the day when the user is using the nebulizer device 102, in response to a biometric indication associated with a physical condition of the user, in response to a predefined user-specific dosing scheme and/or adverse events. The dosing may include a lower dosage of the cannabinoid compound at nighttime. Or the dosing may include a higher dosage of the flavor compound when the user is using the nebulizer device after a typical lunch or dinner time. In some embodiments, the user device 110 is in communication with a wearable device, such as a smartwatch or a wireless wristband (e.g., a fitness wristband). The wearable device may be configured to track one or more biometric indications that are associated with the user's physical condition. Such tracked biometrics may include heart rate, body temperature, sleep profile, activity level, etc. The user device 110 may be further configured to automatically adjust the dosing based on the biometric indication. For example, if the user's heart rate is above a certain threshold level the user device 110 automatically lowers the dosage of the cannabinoid compound to be administered. As another example, if the user's sleep profile from a previous night indicates that the user has not slept well, the user device 110 automatically either lowers or increases the dosage of the cannabinoid compound to be administered.

In some embodiments, the user device 110 includes a user device GUI 114 that may either accept inputs from users or facilitate outputs to the users or may perform both actions. In one case, a user can interact with the interface(s) using one or more user-interactive objects and devices. The user-interactive objects and devices may comprise user input buttons (e.g., the button 126), switches, knobs, levers, keys, trackballs, touchpads, cameras, microphones, motion sensors, heat sensors, inertial sensors, touch sensors, or a combination of the above. The interface(s) may either be implemented as a Command Line Interface (CLI), a GUI, a voice interface, or a web-based user interface. The user device GUI 114 may facilitate the user to input data related to the composition of cannabinoid and flavor compounds in a desired proportion.

In some embodiments, the user device 110 includes a user device application 116 (referred to as "user device app 116"), which may run on the user device 110. In one case, the user device app 116 is a mobile application. In another case, the user device app 116 is a web application. The user device app 116 may provide the graphical user interface (GUI) 112 to the user for various operations such as, but not limited to, displaying the user's profile, tracking the usage of the device over time, logging the dose administered to the user, tracking the dose regimen of the user, and/or enabling the user to communicate with their physician or healthcare provider. In some embodiments, the user can use the user device app 116 to track the dosing. For example, the user device app 116 may provide a display that shows the total dose provided to the user, the maximum dose for a particular day, and/or the dose regimen over previous days. In some embodiments, the user can use the user device app 116 to enter subjective measures that relate to the dosing, such as pain levels, intoxication levels, etc. In some embodiments, the user may request the caregiver (e.g., the caregiver device 118, physician, etc.) to modify the daily dose based on the subjective information. For example, the user can request the caregiver to increase the dose of cannabinoids based on the increased pain level. In another embodiment, the user may modify their dose. In some embodiments, the user device app 116 may facilitate the user to reorder flavor or cannabinoid cartridges.

Figure 2A:
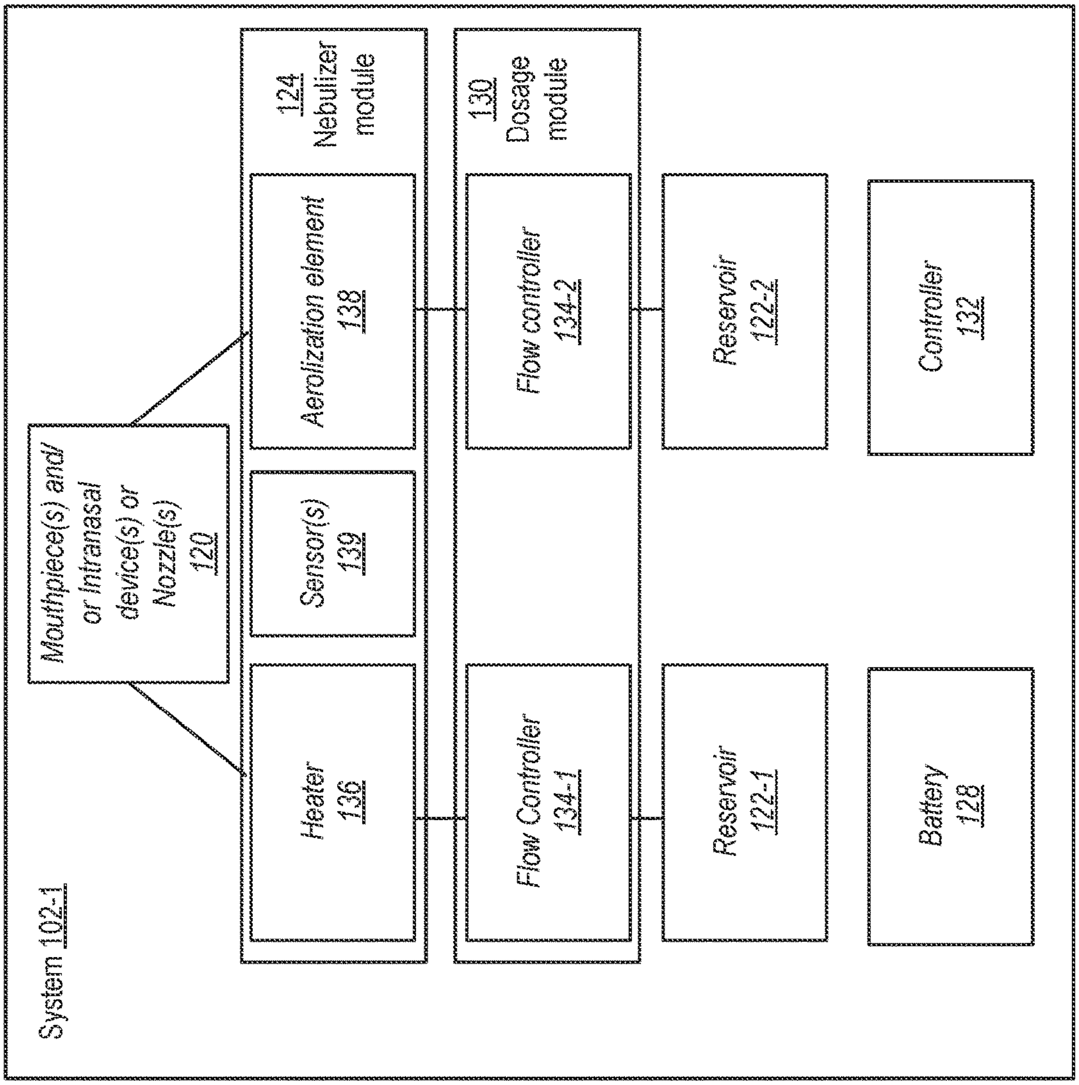
FIG. 2A illustrates a block diagram of the nebulizer device shown in FIG. 1, in accordance with some embodiments.

FIG. 2A illustrates a block diagram of the nebulizer device 102, in accordance with some embodiments. As described above, the nebulizer device 102 is configured to produce inhalable cannabinoid mixtures and control the number and/or amount of cannabinoid and flavor compounds in the mixture. As shown in the nebulizer device 102 in FIG. 2A, the reservoirs 122 include two or more separate reservoirs or cartridges (e.g., a first reservoir 122-1 and a second reservoir 122-2 in FIG. 2A). In some embodiments, the first reservoir may contain a first composition (e.g., the cannabinoid compound) and the second reservoir may contain a second composition (e.g., the flavor compound). The first composition may comprise cannabinoids in a vaporizable or aerosolizable liquid, which may also include carrier or diluent substances, for example, propylene glycol and vegetable glycerin. The second composition may contain a flavor compound, a plurality of flavor compounds, or other compounds, such as pharmaceuticals, in a vaporizable or aerosolizable composition.

In some embodiments, the reservoirs 122 are included in a cartridge that may be removable. For example, a cartridge includes two or more reservoirs, where each of the reservoirs includes a predetermined compound. The cartridge may include, for example, one reservoir including a cannabinoid compound and one, two, or more reservoirs including flavor compounds. In some embodiments, the first reservoir 122-1 and the second reservoir 122-2 are connected to a power source (e.g., one or more batteries 128). The reservoirs may be connected to a single power source or to different power sources.

In some embodiments, the dosage module 130 of a nebulizer device 102 is configured to deliver and control a flow of the liquids from the reservoirs 122 to the nebulizer module 124, thereby controlling the amount of liquids provided to the nebulizer module 124. The dosage module 130 includes one or more flow controllers 134 (e.g., flow controllers 134-1 and 134-2) for individually controlling the flow of the liquid from the first reservoir 122-1 and the flow of the liquid from the second reservoir 122-2. A flow may include one or more of a dial, a valve, or a similar component regulating device for controlling the amount of flavor compound by actuating the opening or closing of a valve or multiple valves. The flow controller may include one or more fluidic pumps. For example, the dosage module 130 includes a single fluidic pump having two pathways for individually controlling the flow of the liquids of the first reservoir 122-1 and the amount of the flavor compound introduced into the output stream. As shown in FIG. 2A, flow controller 134-1 is coupled with reservoir 122-1 and is configured to control the flow of the liquids from reservoir 122-1 to nebulizer module 124. Flow controller 134-2 is coupled with reservoir 122-2 and is configured to control the flow of the liquids from reservoir 122-2 to nebulizer module 124.

In another case, the nebulizer device 102 may include cartridges having other additives and pharmaceutical compositions added to the existing cartridges. Thus, the nebulizer device 102 may include multiple cartridges, each having different vaporizable liquid compositions according to like properties or similar characteristics. The nebulizer device 102 may determine a dosing schema based on a profile created by the user (i.e., the proportion of cannabinoids with respect to a flavor compound or composition). In some embodiments, the dosing schema includes varying the proportions of cannabinoids and the flavor compound or composition while administering the cannabinoids and the flavor compounds or compositions to the user.

The nebulizer device 102 can communicate with components of the system 100. The nebulizer device 102 can wirelessly receive, for example, dosing schemes, machine learning models/programs, settings (e.g., user settings, configuration settings, manufacturing setting, etc.), software updates, control programs, or the like. The nebulizer device 102 can wirelessly transmit information (e.g., nebulizer device information, authentication information, etc.), data (e.g., sensor readings, substance data, etc.), settings (e.g., user inputted settings, automatically generated settings, etc.), or the like.

In some embodiments, the nebulizer module 124 includes one or more nebulizer elements that are different from each other. The nebulizer elements are configured to transform liquids to aerosols (e.g., aerosols or mist) that can be inhaled by the user. The nebulizer elements can include heating elements or non-heating elements (e.g., ultrasonic nebulizers, jet nebulizers, or mesh nebulizers). The type of the nebulizer element is selected based on the liquid to be nebulized. As described above, some cannabinoids, such as THCA, require a significant amount of heat to drive the chemical decarboxylation process which produces neutral or decarboxylated cannabinoids (e.g., THC). Therefore, a reservoir for storing cannabinoid compounds is coupled with a heating element configured for heating the cannabinoid compound to a controlled temperature that allows evaporation of the cannabinoid compound. In contrast, flavor compounds require a low-heat nebulizer to avoid the generation of harmful byproducts. Therefore, a reservoir for storing flavor compounds is coupled with a low-heat aerosolization element. In some embodiments, the nebulizer module 124 includes a single nebulizer element having two pathways and/or two mechanisms for nebulizing the liquids of the first reservoir 122-1 and the second reservoir 122-2 individually.

The nebulizer device 102 may, thereby, provide a solution to avoid lung irritation and other potential lung hazards by allowing the nebulizer or alternative aerosolization activator to introduce the flavor composition into the output stream or multiple output streams while exposing the flavor composition to little or no heat. In FIG. 2A, the first reservoir 122-1 is coupled (e.g., fluidically coupled), either directly or via the dosage module 130, to heating element 136 to volatilize the first composition stored in the first reservoir 122-1. The second reservoir 122-2 is coupled (e.g., fluidically coupled), either directly or via the dosage module 130, to aerosolization element 138 to atomize or nebulize the second composition stored in the second reservoir 122-2. The nebulizer device 102 can include one or more sensors 139 for analyzing or detecting, for example, compositions of substances (e.g., liquids, inhalants, vapors, etc.), temperatures, chemicals, smoke, particles, viscosities, etc. The sensor(s) 139 can be volatile organic compound (VOC) sensors configured to detect one or more VOCs and send signals of VOC detection (e.g., presence or concentration of VOCs(s)) to the controller. In some embodiments, the sensor(s) 139 can detect flavor chemicals that have volatized into harmful chemicals based on, for example, detection of the harmful chemicals, temperature of fluid flows, and/or fluid flow rates. In some embodiments, output from the sensor(s) 139 can be used to determine a classification of the substance, a type of aerosolizable material (e.g., liquid to be aerosolized) and/or aerosol, a mixture of vaporizable/aerosolizable substances, temperatures (e.g., ambient temperature, feed liquid temperatures, inhalant temperatures, vapor temperatures, aerosol temperatures, temperature of heating element(s), etc.), concentrations, quantities (e.g., volumes of liquid or gas), toxicity, pH, densities (e.g., vapor density), particle sizes (e.g., maximum/minimum particle sizes, average particle sizes, etc.). Example sensors 139 include inhale sensors, temperature sensors, infrared sensors, smoke detectors, chemical sensors, flow rate detectors, pressure sensors, current detectors, vapor sensors, vapochromic sensors, gas chromatograph sensor, particle detectors, or the like. Inhale sensors can include one or more airflow sensors to detect air movement in one or more directions. One or more of the sensors 139 can be incorporated into the mouthpiece(s) 120, dosage module 130, flow controllers 134, reservoirs 122, or other devices or components disclosed herein. The number, locations, and configuration of the sensors 139 can be selected based on the desired detection capability of the device 102. In some embodiments, the controller 132 can be programmed to automatically adjust dosages of the respective compounds in the mixture of aerosol cannabinoid, may be automatically adjusted based on the user's preferences, sensor output, biometric data, etc. In some implementations, dosages are adjusted over time while the user is periodically or continuously inhaling the aerosol cannabinoid mixture. For example, the dosages may be adjusted based on the user's preferences, real-time biometric indications, or other parameters (e.g., time of day). This provides an automated and convenient way for the user to enjoy inhaling the user-specific aerosol cannabinoid mixture.

In some embodiments, each of the reservoirs 122 includes a separate heating element, thereby allowing the creation of a combined output stream containing both vaporizable compositions (e.g., active ingredients and a flavor composition). In another embodiment, the nebulizer device 102 may comprise a multi-reservoir vaporizer with active ingredient control. The vaporizer may be capable of determining the potency/concentration of an active ingredient in a first reservoir 122-1 and modifies the relative amounts of vaporization liquid from the first reservoirs 122-1 and the second reservoirs 122-2 based at least in part on the potency or concentration of an active ingredient (e.g., a cannabinoid compound) in the first reservoirs 122-1. The reservoirs 122 can include replaceable cartridges, refillable containers, or the like.

In some embodiments, the vaporizer is capable of creating a consistent dose of an active ingredient in vapor from a plurality of vaporization liquids with various concentrations of an active ingredient. The nebulizer device 102 may comprise a device for adding additives to a smokable article. In some embodiments, the nebulizer device 102 may be attached to the outlet of a smokable article, and the user may thereby draw smoke through the device causing the device to release additives into the smoke. The additives may include a flavor composition and/or a cannabinoid composition. In some embodiments, a plurality of devices may be combined in-series, such that a first device includes a flavor composition, and a second device includes an active ingredient, for example.

In another embodiment, the nebulizer device 102 may comprise vaporizer reservoirs with a flavor coating either on the inside surface (liquid-touching) or external surface (air-touching) of the reservoir. The vaporizer reservoirs may be capable of receiving a vaporizable liquid that dissolves the flavor coating on the inside surface of the vaporizer reservoirs generating a vaporizable flavor composition, in situ. Alternatively or additionally, the vaporizer reservoirs may have the flavor composition ensconced in a polymeric composition; that is, coated or attached to the external surface of the reservoirs 122 such that friction, such as from the user's fingers, releases the flavor composition into the atmosphere or headspace in close proximity to the user. In another embodiment, one could contemplate a dissolvable flavor product for addition to a vaporization liquid wherein the flavored product may be a pellet or capsule. The dissolvable flavor product may be added to a reservoir of vaporization liquid, the flavored product thereby imparting flavor to the vaporization liquid, resulting in a flavored vaporizable liquid wherein the flavored product may dissolve over time into the vaporization liquid. In another embodiment, the nebulizer device 102 may comprise a vaporizer device with multiple liquid reservoirs in-series. A first reservoir in the series may contain vaporization liquid with an active ingredient (e.g., cannabinoids) and a second reservoir in the series may contain vaporization liquid with a flavor composition or other potentially heat-sensitive components.

The nebulizer device 102 also includes the one or more mouthpieces 120. In some embodiments, the mouthpiece 120 corresponds to a tube or a pipe allowing the user of the nebulizer device 102 to inhale the aerosolized cannabinoid mixture from the nebulized device. In some embodiments, the mouthpiece 120 is enrobed with a flavored coating, or comprised of edible flavor to impart the flavor to the vapor passing through the mouthpiece 120, which may dissolve or aerosolize over time. In another embodiment, the flavor compound may be a filter formed from or impregnated with the flavor composition to impart flavor to the output stream passing through the filter. In some embodiments, the mouthpiece 120 may be coated with a flavor coating, or the mouthpiece 120 may be comprised of edible flavor material which dissolves or aerosolizes over time.

In some embodiments, the one or more mouthpieces 120 correspond to an inhalation interface allowing a user to inhale the aerosolized cannabinoid mixture orally and/or intranasally. The inhalation interface may include a combination of different types of outlets for providing the aerosolized cannabinoid mixture to the user. For example, the aerosolized cannabinoid mixture is released to the air so that the user may inhale the compounds via breathing. As another example, the aerosolized cannabinoid mixture is inhaled via the nose via an outlet compatible with nose inhalation.

In addition to such in-series embodiments where the flavor composition is incorporated into an output stream that is then inhaled, another preferred embodiment would incorporate the flavor composition into a parallel output stream as shown in the "in-parallel" system comprised in FIG. 2A. Such a parallel output stream can then be directed at or into the user's nose with a simple directional nozzle or via an intranasal device. In another embodiment, the parallel output stream comprised of the flavor composition can be expelled into the atmosphere or headspace around the user and thus stimulate the senses of taste and smell of the user without requiring direct inhalation of the output stream by the user.

In an additional embodiment, the vaporizer may contain stackable mouthpieces 120, where each mouthpiece 120 may introduce a different flavor compound, cannabinoid, or other active ingredients. In one case, the nebulizer device 102 may include new cartridges, exchanged with the existing cartridge, having other additives which may include pharmaceutical compositions. The nebulizer device 102 may comprise the stackable mouthpieces 120 for a vaporizer. The stackable mouthpieces 120 may include various flavor compositions, active ingredient compositions, etc., to the output stream which passes through the stackable mouthpieces 120. In another embodiment, the nebulizer device 102 may comprise a vaporizer without flavoring the vaporizer liquid. The method involves placing a flavored filter component at the air inlet of a vaporizer, thus allowing the user to draw air through the flavored filter, which flavors the air before it enters into the vaporizer.

In some embodiments, the nebulizer device 102 further includes the controller 132. The controller 132 includes a memory for storing instructions for operating the nebulizer device 102 and a processor for executing the instruction. The controller 132 may further include a receiver and a transmitter for communicating with the user device 110 and/or the caregiver device 118. The controller 132 is configured to receive instructions, including the dosage scheme described above, from the user device 110. The controller 132 then executes the instructions to operate the nebulizer device 102 to produce and provide cannabinoid compound mixtures to the user based on the received instructions. Executing the instructions includes controlling the dosage module 130 (e.g., including the flow controllers 143-1 and 143-2) and the nebulizer module 124 (e.g., including the heating element 136 and aerosolization element 138) to produce an aerosolized mixture to be provided to the user via the mouthpiece 120. In some embodiments, the nebulizer device 102 additionally includes a database to store the profile for each user based on the user's desired composition, effects, or flavor profile (e.g., a database stored in the memory of the controller 132).

In some embodiments, the nebulizer device 102 may facilitate the testing and/or verification of the contents of the cartridges prior to activating the vaporizer device to ensure that the vaporizable liquid(s) does not contain one or more flavor compounds, or any other compound, which may become hazardous if inhaled or subjected to heat by the vaporizer. The nebulizer device 102 may become locked and provide a notification to the user if an incompatible or hazardous composition or substance is detected.

As described above, the nebulizer device 102 may be in communication with the user device 110 to facilitate the user to set the desired proportion of cannabinoid and flavor composition to the nebulizer device 102 via a user device app 116 on the user device 110 such that the regimen changes based on a change in the desired composition by the user. That is, a change in the desired composition established by the user from 1:4 to 2:4 can produce a new regimen where 2 draws of cannabinoid and 4 draws of flavor compound can occur in every 6 draws. The user device 110 may also help in tracking the usage of the nebulizer device 102 over time. In one case, the nebulizer device 102 may be customized for each user based on the desired composition, effects, and/or flavor profile. For example, the user has created a profile on 12/18/2020 (i.e., profile 1) having the composition of cannabinoid and flavor compound in a proportion of 1:4. This could provide the user with 1 draw of cannabinoid and 4 draws of flavor composition for every 5 total output stream draws. The user has created a second profile on 12/19/2020 (i.e., profile 2) designating the ratio of cannabinoid or cannabinoid composition to flavor compound or flavor composition as 2 parts to 3 parts, respectively. This may change the composition from 1:4 to 2:3 and may provide 2 draws of cannabinoid and 3 draws of flavor compound for every 5 draws for the period the user is using the nebulizer device 102.

In some embodiments, the amount of flavor may be changed by the dosage module 130 of the nebulizer device 102. Hence, a controlled method of drawing the cannabinoid and the flavor compound is facilitated. In some embodiments, the method may include a test to determine if flavor chemicals will volatize into harmful chemicals based on the temperature and airflow of the vaporizer device. In another embodiment, the nebulizer device 102 may comprise a vaporizer using a flavored filter. The filter component is placed between the outlet of a vaporizer and the user's mouth, such that the vapor from the vaporizer must be pulled through the filter, the filter containing flavor compounds that impart flavor to the vapor before entering the user's mouth.

Figure 2B:
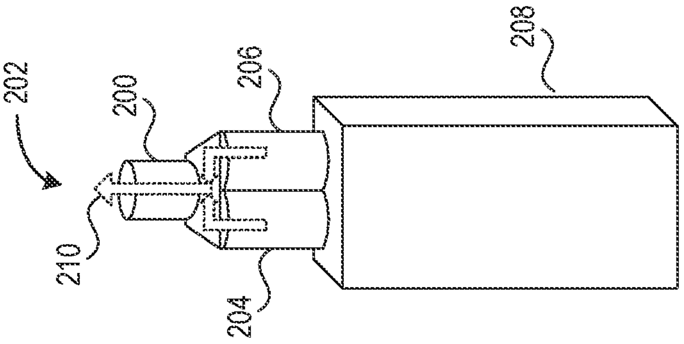
FIG. 2B shows an in-parallel nebulizer device, in accordance with some embodiments.
Figure 2C:
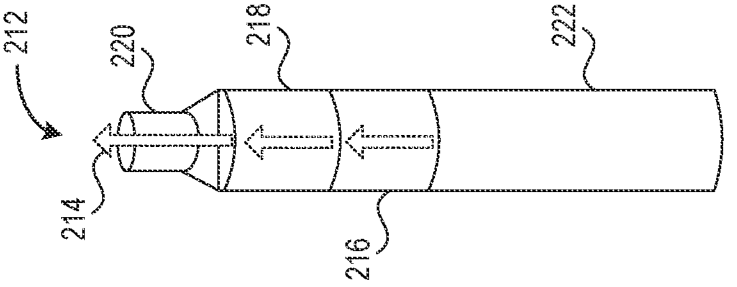
FIG. 2C shows an in-series nebulizer device, in accordance with some embodiments.

FIG. 2B shows an in-parallel nebulizer device 202, in accordance with some embodiments. In some embodiments, the in-parallel nebulizer device 202 corresponds to the nebulizer device 102 described above. The in-parallel nebulizer device 202 includes a mouthpiece 200, a first reservoir 204, a second reservoir 206, a battery 208, and a path of output stream 210. FIG. 2C shows an in-series nebulizer device 212, in accordance with some embodiments. The in-series nebulizer device 212 includes a mouthpiece 220, a first reservoir 216, a second reservoir 218, a battery 222, and a path of output stream 214. In some embodiments, the in-parallel nebulizer device 202 and in-series nebulizer device 212 may comprise other components, such as nebulizer module 124 and the button 126 shown as components of nebulizer device 102. The in-parallel nebulizer device 202 is an exemplary embodiment of a decoupled vapor device in an in-parallel configuration. The first reservoir 204 and second reservoir 206 may contain distinct vapor compositions, which may be, for example, a flavor composition and an active ingredient composition, respectively. Battery 208 may supply power to atomizers located in one or both of first reservoir 204 and second reservoir 206, either synchronously or asynchronously. Supplying power to at least one atomizer generates a vaporized composition that follows the path of output stream 210. Path of output stream 210 shows vapor exiting independently from each of first reservoir 204 and second reservoir 206 before being combined and exiting the in-parallel nebulizer device 202 via mouthpiece 200. In this way, the contents of the first reservoir 204 and the second reservoir 206 may be vaporized independently, at different rates, temperatures, or other vaporization parameters, without affecting the vaporization of the other reservoir. The in-series nebulizer device 212 is an exemplary embodiment of a decoupled vapor device in an in-series configuration. The first reservoir 216 and second reservoir 218 may contain distinct vapor compositions, which may be, for example, a flavor composition and an active ingredient composition, respectively. Battery 222 may supply power to atomizers located in one or both of first reservoir 216 and second reservoir 218, either synchronously or asynchronously. Supplying power to at least one atomizer generates a vaporized composition that follows the path of output stream 214. Path of output stream 214 shows vapor exiting first reservoir 216 and following a vertical path to the second reservoir 206 before exiting the in-series nebulizer device 212 via mouthpiece 220. In this way, the contents of the first reservoir 216 and the second reservoir 206 may be vaporized in-series, wherein a first vapor is generated from a first reservoir 216 and flows into a second reservoir 218, which generates a second vapor which combines with the first vapor, the combined vapor thus exiting the in-series nebulizer device 212 via mouthpiece 220. The first reservoir 216 and second reservoir 218 may require different vaporization parameters, such as vaporizing at different rates, temperatures, or other vaporization parameters. However, heat and vapor from the first reservoir 216 may affect the vaporization of the second reservoir 218. This may be preferred in some embodiments, since, in one example, a second composition in a second reservoir 218 may require less temperature to vaporize than a first composition in a first reservoir 216, the second reservoir 218 may thereby receive partial or sufficient heat from the first reservoir 216 to vaporize the second composition with reduced power or without the need for power from the battery 222. It is generally understood for the purpose of this invention that mouthpiece 200 and/or mouthpiece 220 may be any adaptor to the in-parallel nebulizer device 202 and/or in-series nebulizer device 212 capable of dispersing or dispensing vapor to an orifice or location preferred by the user, and may be, for example, an adaptor for the mouth, nostrils, or environmental dispersion, such as humidifiers or aromatic vaporizers, the in-parallel nebulizer device 202, and/or in-series nebulizer device 212 thereby being capable of oral or inhaled delivery of vapor, intranasal delivery of vapor, ambient or transdermal delivery of vapor, or some combination thereof, respectively.

Functioning of the device database 104 will now be explained with reference to FIG. 3. FIG. 3 shows a screenshot 300 of a display displaying the device database 104, in accordance with some embodiments. The device database 104 is displayed on the GUI 114 coupled to a user device interface module 112 of the user device 110. The device database 104 includes a first composition of cannabinoid and a second composition of flavor compound in x:y proportions, based on the user requirements. The proportion x:y means drawing cannabinoid x times and flavor compound y times for x+y draws, or alternatively, creating a vapor stream that is approximately [(x/(x+y))*100]% cannabinoid formulation and [(y/(x+y))*100]% flavor formulation.

For example, the screenshot 300 of the device database 104 includes the profiles for the user. The profile includes the composition of cannabinoid and flavor composition in the desired proportion of 1:4. This signifies the user draws cannabinoid compounds 1 time and flavor compounds for 4 times for every 5 draws. It can be noted that the user may control the proportion of cannabinoid and flavor compounds via a user device app 116 on the user device 110. The device database 104 may include the flavor profile (i.e., form and volume of flavor compound to be given to the user), as well as the temperatures of cannabinoids and flavors, respectively. A controller, such as a dial, button, or programmatic interface on the user device 110, may be used to control the volume of flavor and/or cannabinoids by controlling the opening or closing of valves in the nebulizer device 102, each valve controlling the rate of flow from a plurality of reservoirs. For example, the device database 104 includes profiles for the user based on the desired composition of cannabinoid and flavor compound for one week along with the flavor profile.

In some embodiments, the ratio of cannabinoids to flavors may also depend on the concentration of cannabinoids and flavors in respective compositions. In some embodiments, the ratio may be based, at least in part, on the potency of the compositions. In some embodiments, the device database 104 may comprise a plurality of profiles corresponding to a user. The profiles may comprise information such as days, composition, and flavor profile corresponding to the user.

For example, for the user, profile 1 corresponds to date 12/18/2020 with the compositions of CBD to flavor in 1:4 ratio and a flavor profile with vapor-liquid of 1 mL. Each reservoir and each component in such reservoirs may be associated with a specific volatilization, vaporization, or aerosolization temperature. For example, a CBD cartridge may be associated with a vaporization temperature of 370° F. and a flavor cartridge may be associated with a vaporization temperature of 215° F. or an aerosolization temperature at room temperature of equal to or less than 150° F. By associating a first and second reservoir with a first and second vaporization temperature, the nebulizer device 102 is capable of producing two output streams at differing temperatures, each temperature thereby optimized to incorporate the associated cartridge contents into the output streams while minimizing the application of unnecessary heat. Importantly, this may prevent certain cartridge contents (e.g., flavor compounds), from being vaporized at a temperature that may create harmful compounds, which may be the case when flavor compounds and cannabinoids are mixed together.

Methods

Figure 4:
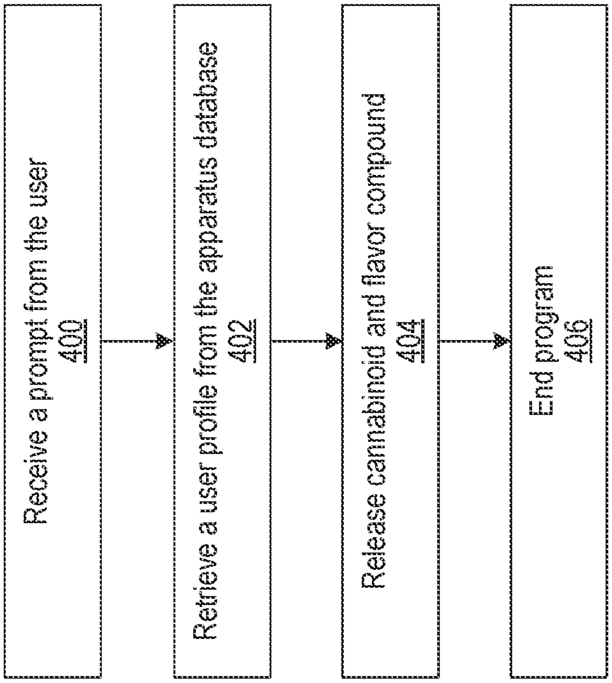
FIG. 4 shows a flowchart describing a method for operating a nebulizer device, in accordance with some embodiments.

Methods and operations performed by the nebulizer device 102 will now be explained with reference to FIG. 4. FIG. 4 shows a flowchart describing a method for operating the nebulizer device 102, in accordance with some embodiments. In some embodiments, the dosage module 130 receives a prompt from the user to activate the nebulizer device 102. For example, the dosage module monitors the communications received from the user device 110, and the nebulizer device 102 is activated in response to a trigger received from the user device 110. In some embodiments, the dosage module 130 may receive the prompt when the user logs in to the user device app 116 on the user device 110 to activate the nebulizer device 102. For example, dosage module 130 receives a prompt when the user logs in to the user device app 116 on the user device 110 to activate the nebulizer device 102, at step 400.

In some embodiments, the dosage module 130 retrieves a user profile from the device database 104 associated with the user. In some embodiments, the user profiles may be based on information provided by a caregiver (e.g., the caregiver device 118). For example, the dosage module 130 retrieves 'the user's profile (i.e., profile 1) from the device database 104 associated with the user. Profile 1 corresponds to date 12/18/2020 with the compositions of CBD to flavor in 1:4 ratio and a flavor profile with vapor-liquid of 1 mL, at step 402.

Based on the retrieved user profile, the dosage module 130 may release, at step 404, the cannabinoid and flavor compound. In some embodiments, the cannabinoid may be released based on heating at an appropriate temperature by the vaporizing element and the flavor compound may be released by the nebulizer module 124 or nebulizer. For example, the dosage module 130 releases the desired composition of cannabinoid and flavor compound in a proportion of 1:4 (i.e., 1 draw of cannabinoid and 4 draws of flavor compound for every 5 draws) such that each draw equates to roughly the same volume of gaseous vapor/aerosol, at step 404.

In some embodiments, the method further includes, prior to releasing the cannabinoid and flavor compound, obtaining information regarding a compound cartridge inserted in the nebulizer device 102. The cartridge includes the reservoirs 122 (e.g., reservoirs 122-1 and 122-2). The information may include the type of the compounds, the concentration, the volume, etc., of the compounds included in the reservoirs 122. The information may be obtained, for example, based on an identification code associated with the cartridge. In some embodiments, the information is obtained by reading the identification code associated with the cartridge (e.g., using a camera of the user device 110). In some embodiments, the information is obtained by a user input on the user device 110. In some embodiments, the obtained information regarding the compound cartridge is used for determining the dosage scheme for releasing the cannabinoid flavor compounds. The method then includes setting the ratio of the cannabinoid and the flavor compounds to be released by the nebulizer device 102.

Thereafter, the program ends, at step 406.

Figure 5:
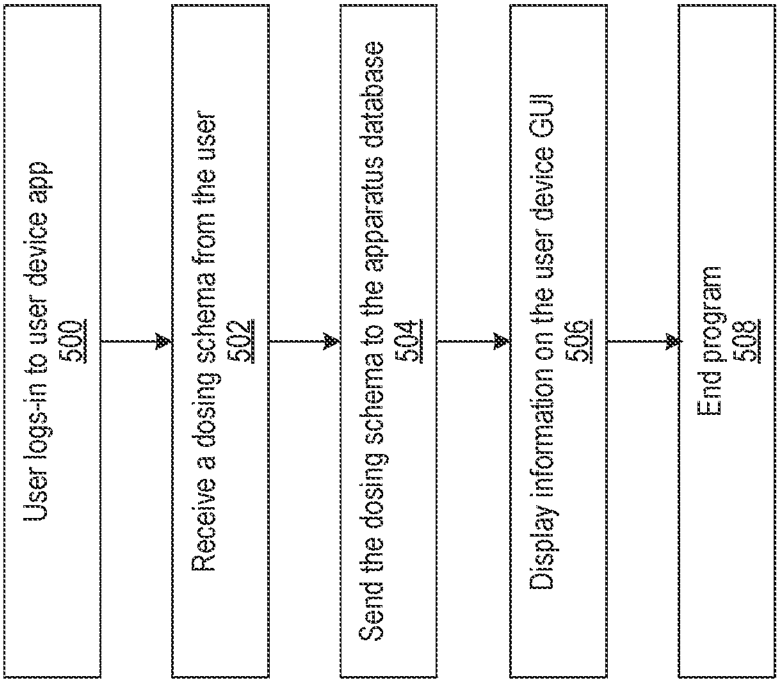
FIG. 5 shows a flowchart describing a method for operating a user device interface module of a user device, in accordance with some embodiments.

Methods and operations performed by the user device interface module 112 of the user device 110 will now be explained with reference to FIG. 5. FIG. 5 shows a flowchart describing a method for operating the user device interface module 112 of the user device 110, in accordance with some embodiments.

The process begins when the user device interface module 112 is triggered when the user logs in to the user device app 116, on the user device 110. The user device interface module 112 may facilitate the user to access the nebulizer device 102 and create a dosing schema associated with the user, at step 500.

The user device interface module 112 may receive, at step 502, a dosing schema from the user. In some embodiments, the dosing schema may comprise a composition of the cannabinoid and the flavor compound. For example, the user device interface module 112 receives the dosing schema containing compositions of cannabinoid and flavor compound in a proportion of 1:4, and a flavor profile (i.e., 1 mL flavor compound in vapor-liquid form) from the user, at step 502.

The user device interface module 112 may send, at step 504, the dosing schema to the device database 104. For example, the user device interface module 112 sends the dosing schema containing compositions of cannabinoid and flavor compound in a proportion of 1:4, and a flavor profile (i.e., 1 mL flavor compound in vapor-liquid form) to the device database 104, at step 504.

The user device interface module 112, at step 506, may display information on the user device GUI 114 (e.g., the screenshot 300 of the GUI 114 described with respect to FIG. 3). For example, the user device interface module 112 may display information, such as the user profile, composition of cannabinoid and flavor compound, etc., on the user device GUI 114. In some embodiments, the user device interface module 112 may display the total dose provided to the user, the maximum dose for a particular day, or the dose regimen over previous days.

In some embodiments, the user device interface module 112 may facilitate the user to track the dose of cannabinoid and the flavor compound. The user device interface module 112 may facilitate the user to enter subjective measures that relate to dosing, pain levels, intoxication levels, etc. Furthermore, the user device interface module 112 may facilitate the user to request a caregiver to modify the daily dose (i.e., increase or decrease the total cannabinoids allowed) based on the subjective information (such as too much pain, too much intoxication, etc.), at step 506. Thereafter, the program ends, at step 508.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Computing Systems and Devices

FIG. 6 is a block diagram of a computer system 600 that may be used to implement features of some embodiments of the disclosed technology. In some embodiments, the computing system corresponds to the user device 110, the caregiver device 118, and/or the nebulizer device 102. The computing system 600 may be used to implement any of the entities, components, or services depicted in the examples of FIGS. 1-5 (and any other components described in this specification).

The computing system 600 may include one or more central processing units ("processors") 605, memory 610, input/output devices 625 (e.g., keyboard and pointing devices, buttons, display devices, etc.), storage devices 620 (e.g., disk drives), and network adapters 630 (e.g., network interfaces) that are connected to an interconnect 615. The interconnect 615 is illustrated as an abstraction that represents any one or more separate physical buses, point-to-point connections, or both connected by appropriate bridges, adapters, or controllers. The interconnect 615, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2B) bus, or an Institute of Electrical and Electronics Engineers (IEEE) standard 1394 bus.

The memory 610 and storage devices 620 are computer-readable storage media that may store instructions that implement at least portions of the described technology. In addition, the data structures and message structures may be stored or transmitted via a data transmission medium, such as a signal on a communications link. Various communications links may be used, such as the Internet, a local area network, a wide area network, or a point-to-point dial-up connection (e.g., the Bluetooth connection). Thus, computer-readable media can include computer-readable storage media (e.g., "non-transitory" media) and computer-readable transmission media.

The instructions stored in memory 610 can be implemented as software and/or firmware to program the processor(s) 605 to carry out the actions described above. In some embodiments, such software or firmware may be initially provided to the processing system 600 by downloading it from a remote system through the computing system 600 (e.g., via network adapter 630).

The technology introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

The input/output devices 625 may include input devices such as keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers. Devices may include a combination of multiple input or output devices, including, for example, touch screens, physical buttons (e.g., the button 126), microphones, fingerprint readers, accelerometers, vibration devices, etc. Some devices allow gesture recognition inputs by combining some of the inputs and outputs. Some devices allow for facial recognition, which may be utilized as an input for different purposes, including authentication and other commands. Such devices allow for voice recognition and inputs, including, for example, Microsoft KINECT, SIRI for iPhone by Apple, Google Now, or Google Voice Search. Additional mobile devices have both input and output capabilities, including, for example, haptic feedback devices, touchscreen displays, or multi-touch displays. Touchscreen, multi-touch displays, touchpads, touch mice, or other touch sensing devices may use different technologies to sense touch, including, for example, capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, for example, pinch, spread, rotate, scroll, or other gestures. Some touchscreen devices, including, for example, Microsoft PIXELSENSE or Multi-Touch Collaboration Wall, may have larger surfaces, such as on a table-top or a wall, and may also interact with other electronic devices. Some I/O devices, display devices, or groups of devices may be augmented reality devices.

Figure 7:
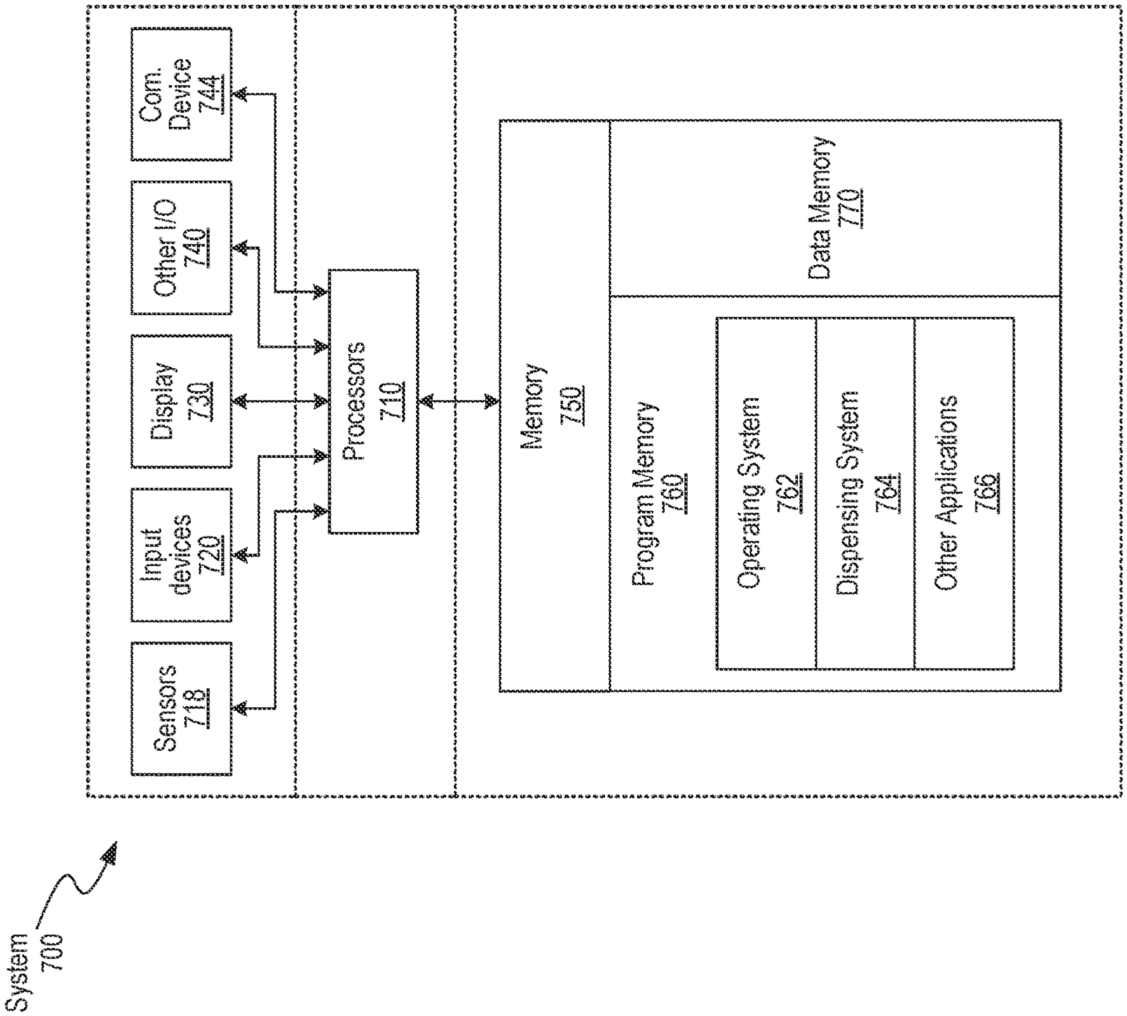
FIG. 7 is a block diagram illustrating an overview of a system on which some implementations of the disclosed technology can operate, in accordance with some embodiments.

FIG. 7 is a block diagram illustrating an overview of a system 700 on which some implementations of the disclosed technology can operate. The system 700 can include one or more sensors 718 and input devices 720 that provide input to the processor(s) 710 (e.g., CPU(s), GPU(s), HPU(s), etc.), notifying it of, for example, adverse event(s), operation, and/or actions. The input can be mediated by a hardware controller that interprets the signals received from the input device and communicates the information to the processors 710 using a communication protocol. Processors 710 can be a single processing unit or multiple processing units in a device or distributed across multiple devices. Processors 710 can be coupled to other hardware devices, for example, with the use of a bus, such as a PCI bus or SCSI bus. The processors 710 can communicate with a hardware controller for devices, such as for a display 730. Display 730 can be used to display text, graphics, indicators, etc. In some implementations, display 730 provides graphical and/or textual visual feedback (e.g., liquid levels, cartridge type, dosage information, etc.) to a user. In some implementations, display 730 includes the input device as part of the display, such as when the input device is a touchscreen. Examples of display devices are: an LCD display screen, an LED display screen, a projected or augmented reality display, such as a heads-up display device or a head-mounted device, and so on. For example, an augmented reality display can display dosing information in a virtual environment (e.g., a virtual environment for mediation, therapy, etc.). Other I/O devices 740 can also be coupled to the processor, such as a user device (e.g., user device 710), network card, video card, audio card, USB, firewire or other external device, camera, speakers, etc. In some implementations, the device 100 also includes a communication device 740 capable of communicating wirelessly or wire-based with a network node. The communication device can communicate with another device or a server through a network using, for example, TCP/IP protocols. The system 700 can utilize the communication device to distribute operations across multiple network devices.

The processors 710 can have access to a memory 750 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 750 can include program memory 760 that stores programs and software, such as an operating system 762, dispensing or dosing system 764 ("dispensing system 764"), and other application programs 766. Memory 750 can also include data memory 770, e.g., authentication information (e.g., cartridge authentication, user authentication, liquid composition authentication, etc.), biometric data, compound data, cartridge data, notification data, user personal health information, configuration data, settings, user options or preferences, etc., which can be provided to the program memory 750 or any element of the device 700.

The systems (e.g., systems 600 and 700) can be part of the system 100 of FIG. 1, system 102-1 of FIG. 2A, and other systems or components disclosed herein. For example, the controller 132 of FIG. 1 can include all or a portion of the systems 600 (FIG. 6) or 700 (FIG. 7). In some embodiments, the systems 600 (FIG. 6) or 700 (FIG. 7) are distributed between multiple devices, such as dispensing devices, user devices, caregiver devices, etc.

The systems and devices disclosed herein can be configured for machine learning model(s). The machine learning models can be of various types, such as Convolutional Neural Networks (CNNs), other types of neural networks (e.g., fully connected), decision trees, forests of classification trees, Support Vector Machines, etc. Machine learning models can be trained to produce particular types of results, operations, etc. For example, a training procedure can include obtaining suitable training items with input associated with a result, applying each training item to the model, and updating model parameters based on comparison of model result to training item result. The machine learning model(s) can be generated by, for example, the cloud system 108 of FIG. 1 using data from the database 104 of FIG. 3. Example machine learning models are discussed in connection with FIG. 8.

Figure 8:
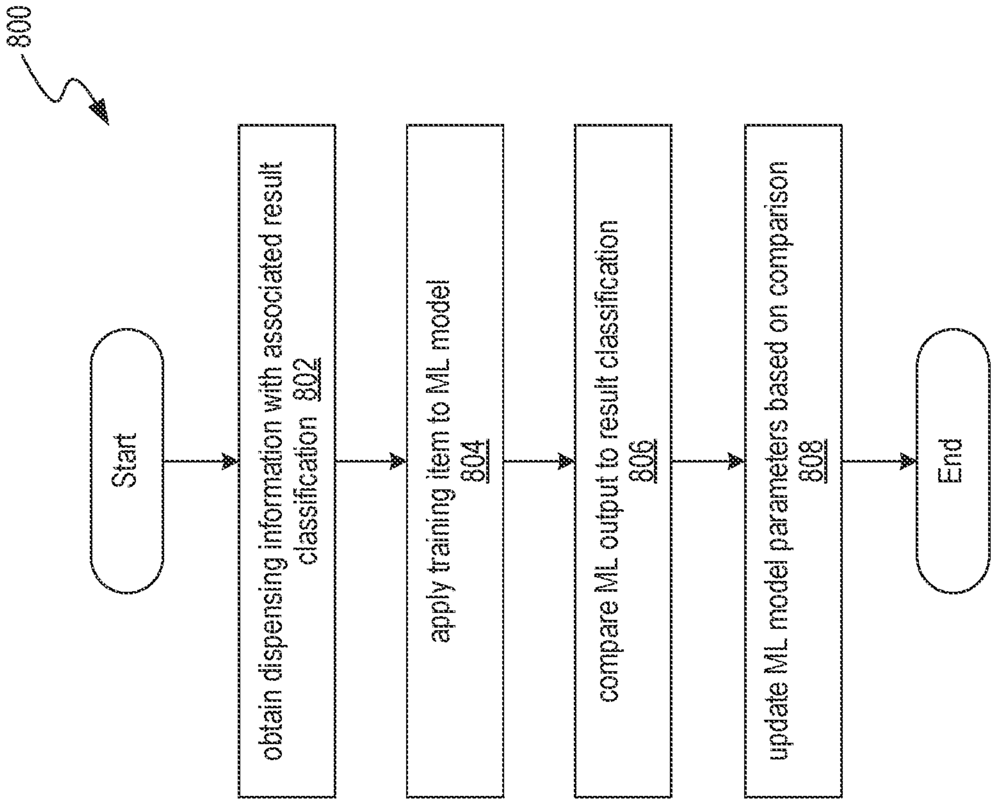
FIG. 8 illustrates a flowchart showing a method for training a machine learning model, in accordance with some embodiments.

FIG. 8 illustrates a flowchart showing a method 800 for training a machine learning model, in accordance with some embodiments. Machine learning models, such as neural networks, can be trained to produce types of results. A neural network can be trained by obtaining, at block 802, a quantity of "training items," where each training item includes input similar to input the model will receive when in use and a corresponding scored result. At block 804, the input from each training item can be supplied to the model to produce a result. At block 806, the result can be compared to the scored result. At block 808, model parameters can then be updated, based on how similar the model result is to the scored result and/or whether the score is positive or negative. The method 800 can be used to generate one or more trained machine learning models for outputting any of the following: dosing schemes, therapeutically effective amounts for a specific user, a predicted flavor, prediction of a future value of the health parameter within a period of time, therapeutic effect, etc. The steps of the method 800 can be selected based on the inputs and desired output and are discussed below.

At block 802, model input can include, without limitation, stored data (e.g., data from database 104 of FIG. 3), dispensing information, including taste preferences, user-specific input can include sensitivity level(s) (e.g., taste sensitivity, active agent sensitivity), caregiver input, user input, dispensing parameters (e.g., temperature, flow rates, etc.), and so forth. The training data input can be classified and/or paired with results to create training items. The classification can be selected based on the model characteristics and output. The results for training items can be, for example, user feedback to model outputs, healthcare provided suggestion feedback (e.g., whether the healthcare accepted model provided recommendations completely, or made certain changes, or disregarded), user rating or scoring of doses, biometric data analyzed to determine results, the existence of certain positive or negative user experiences, or the like. The product input can include, without limitation, flavor characteristics (e.g., sweet, sour, bitter, umami, etc.), physiological and psychological characteristics (e.g., body high, mental high, etc.), health benefits (e.g., anxiety relief, muscle spasm relief, etc.), sub-species of cannabis plant (e.g., *sativa*, indica, hybrid, etc.), or the like. Other input to the user experience feedback may include objective data, such as personal data collected by biometric or wearable devices. The user feedback (e.g., flavor feedback, experience feedback, etc.) may result in refined personal dosing schemes, recommended products, recommended settings, etc. The data discussed in connection with FIG. 3 can be used as model input, model selection, etc. The input, subject scoring, and other information can be collected via, for example, a user device (e.g., user device 110 of FIG. 1), input/output devices (e.g., input/output devices 625 of FIG. 6, input devices 720 of FIG. 7, etc.). In some embodiments, user feedback is aggregated. Aggregated user feedback may be used to develop and refine a heuristic algorithm to provide schemes, recommendations, etc., to new users, users using new substances, or the like.

At block 804, input from each training item can be supplied to the model to produce a result or output. The output can be converted to arrays of integers that, when provided to the machine learning model, produce values that specify dosing schemes, device settings, etc. Any number of models can be generated to recommend dosing schemes, products for purchase, recommended flavoring products, etc.

At block 806, results can be compared to the scored result or result classification. For example, result dosing schemes can be compared to actual dosing schemes used by users that produced the training item. The model can correlate composition information to predicted user experience. The composition information can indicate flavor compound, flavor concentration, volume, tobacco concentration, nicotine concentration, and/or whether a cannabis product is THC (tetrahydrocannabinol) dominant, THCA (tetrahydrocannabinolic acid) dominant, CBD (cannabidiol) dominant, CBDA (cannabidiol acid) dominant, THC/THCA-CBD/CBDA balanced, or the like or alternatively can include composition information in terms of mass percentages (e.g. THC=80%, CBD=5% and CBG=2%).

At block 808, model parameters can be updated, based on how similar the model result is to the scored result and/or whether the score is positive or negative. The model parameters can then be adjusted so the model output is more like the prior dosing scheme and user experience if that prior user experience was a success or less like the prior dosing scheme, if the prior user experience was unsuccessful (e.g., unwanted flavor, unwanted experience, etc.). The amount of adjustment to the model parameters can be a function of how different the model prediction was from the actual dosing scheme used and/or the level of success or failure of the product usage. Machine learning models can be trained to produce various results, such as to provide minimum flavor, achieve a flavor profile, determine dosing schemes (e.g., constant or variable dosing schemes), target temperatures, target inhalant characteristics (e.g., ratios of substances, particle size, etc.), or the like. Models can be grouped or classified based on user characteristics, such as user sensitivity.

The method 800 can generate dispensing schemes based on a user's profile, previous sensor data for that user, and/or information and/or sensor data from a plurality of other users. In some embodiments, a health state is quantified as a score or metric representing the user's overall health status and/or risk, which can be generated based on any suitable combination of sensor data and/or other data. In some embodiments, user-specific setting or recommendations may be based upon, for example, the health state, specific user's experience feedback, etc. The user experience feedback may query the user for a variety of parameters. Questions may solicit information regarding, for example, flavor characteristics (e.g., intensity, bitterness, sweetness, umami, etc.), a degree of hunger, euphoria, queasiness, relaxation, and/or other such subjective aspects. For example, a model can be trained using sets of user feedback, flavor profiles, dosage information, composition information, volumes, temperatures (e.g., active ingredient temperatures, flavor compound temperatures, etc.), type of administration (e.g., vapor liquid, filter, mouthpiece, etc.), and corresponding scores for usage.

In some embodiments, multiple machine learning training procedures can be performed. Example procedures can include obtaining suitable training data set associated with a result, applying each training data set to the model, and updating model parameters based on comparison of model result to training set result. Each model can be design for a different result. A neural network can be trained by obtaining a quantity of "training items or data set," where each training item or data set includes input similar to input the model will receive when in use and a corresponding scored result. The input from each training item/data set can be supplied to the model to produce a result. The result can be compared to the scored result. Model parameters can then be updated based on how similar the model result is to the scored result and/or whether the score is positive or negative. A training procedure can include clustering, predictive analysis, etc. as discussed above. The training procedure can be selected based on the amount, quality, and/or characteristics of the data.

In an illustrative embodiment, any of the operations, processes, etc., described herein can be implemented as computer-readable instructions stored on a computer-readable medium. The computer-readable instructions can be executed by a processor of a mobile unit, a network element, and/or any other computing device.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like. For example, the nebulizer device 102 of FIG. 1 can be operational with a computing system environment with one or more computers or gaming consoles. When a user plays a video game, the operation of the nebulizer device 102 can be controlled based on the levels passed, score, and other information related to the video game.

Exemplary Embodiments of the Present Disclosure

In accordance with some embodiments, a portable nebulizer device (e.g., the nebulizer device 102 in FIGS. 1 and 2A) for administering aerosol cannabinoid mixtures to a user includes a mouthpiece (e.g., the mouthpiece 120), a first reservoir, and a second reservoir (e.g., the reservoirs 122-1 and 122-2). The second reservoir is separate from the first reservoir. The device also includes a nebulizer module (e.g., the nebulizer module 124) fluidically coupled to the first reservoir and the second reservoir. The nebulizer module is configured to receive a first dosage of the first liquid from the first reservoir and a second dosage of a second liquid from the second reservoir. The nebulizer module is also configured to transform the received first liquid into an inhalant and the received second liquid into an aerosol that are provided to the user through the mouthpiece. The device further includes a dosage module (e.g., the dosage module 130) configured to independently control delivery of the first liquid and the second liquid to the nebulizer module to set a ratio between the first dosage of the first liquid and the second dosage of the second liquid. In some embodiments, the dosage module is configured to automatically set the first dosage and the second dosage based on the user's preference (e.g., based on a user input) or time of the day (e.g., morning, afternoon, night time). The device thereby controls a composition of an aerosol cannabinoid mixture administered to the user. The aerosol cannabinoid mixture includes the inhalant and the aerosol.

In some embodiments, the second liquid includes a flavor compound that is detectable by the user (e.g., via taste) when the user receives the cannabinoid mixture through the mouthpiece. The second liquid may be transformed into the aerosol without heating so that the flavor compound does not thermally degrade while being transformed into the aerosol thereby avoiding transformation of the flavor compound to a potentially hazardous compound. The user can set the amount of second liquid by, for example, gradually increasing the amount of second liquid being delivered, delivery rate (e.g., volumetric flow rate), etc. The user can input (e.g., via a mobile application, input device on the nebulizer device 102, etc.) when the user, for example, taste the flavor compound, taste level (e.g., mild flavor, medium flavor, strong flavor, etc.), taste a desired level of the flavor compound, taste an excessive amount of the flavor compound, and/or additional taste-related input. The systems disclosed herein can store the user-inputted taste setting and then automatically set the dispensing settings based on, for example, the characteristics of the second liquid, flavor compound, number of taste liquids, etc. This allows the second liquid to be used with different types of first liquids. In some embodiments, the nebulizer device 102 can determine dispensing settings for the second liquid based on comparisons to a user's usage history, such as user input for previously consumed second liquids. When a user installs a new container holding a second liquid, the characteristics of the second liquid can be compared to previously consumed flavor compounds. The dosing settings can be generated to match, or rematch (or be similar to), dosing settings for previously consumed flavor compounds. This allows nebulizer device 102 to determine dosing settings to provide a desired taste to the user based the user's usage history. The user can periodically provide user settings to compensate for changes of preferences, taste, or the like. In some embodiments, a group of prior user data can be analyzed to determine recommended taste settings.

In some embodiments, the dosage module is configured to automatically adjust the first dosage of the first liquid and the second dosage of the second liquid while the aerosol cannabinoid mixture is being administered to the user. The adjusting may be performed by individually controlling the flow of the liquids from the reservoirs 122 to the nebulizer module 124 by the flow controllers 134. In some embodiments, the dosage of the first liquid and the dosage of the first liquid are reduced over time. In some embodiments, the first dosage of the first liquid (e.g., the cannabinoid) is reduced while maintaining the second dosage of the second liquid (e.g., the flavor compound, aroma compound, etc.), or vice versa. For example, the user may first wish to inhale a combination that includes a stronger effect of the flavor and then reduce the flavor effect over time. In some embodiments, the user is thereby not required to adjust the dosages of the cannabinoid and flavor compounds while using the nebulizer device. Instead, the device can automatically adjust the dosages.

In some embodiments, automatically adjusting the first dosage of the first liquid and the second dosage of the second liquid is performed in response to a biometric indication associated with a physical condition of the user. In some embodiments, the biometric indication includes a heart rate, a body temperature, a sleep profile, or an activity level that can be measured by a wearable device (e.g., a smartwatch or a wireless wristband). The device may adjust the first dosage and the second dosage in accordance with the received biometric indication. For example, if the heart rate of the user increases over a certain threshold limit while the user is using the nebulizer device, the device may decrease the dosage of the cannabinoid compound. As another example, if the user's sleep quality from a previous night has indicated that the user has not slept well, the nebulizer device may automatically change the dosage of the cannabinoid compound to be administered.

In some embodiments, automatically adjusting the first dosage of the first liquid and the second dosage of the second liquid is performed in response to a predefined user-specific dosing scheme. For example, the user may predefine a user-specific dosing scheme (e.g., as described with respect to FIG. 3) that includes initial dosages for the cannabinoid and flavor compounds, and how to increase or decrease the dosages over time while the user is using the nebulizer device.

In some embodiments, the second temperature is maintained below 125° F. (e.g., below approximately 50° C.). In some embodiments, the second temperature is maintained below 110° F., below 100° F., below 90° F., or below 80° F. In some embodiments, the second temperature is maintained at about room temperature (e.g., at about 75° F.).

In some embodiments, the nebulizer module comprises a heater (e.g., heating element 136 in FIG. 2A) configured to transform the first liquid to the inhalant at a first temperature aerosolization element (e.g., the aerosolization element 138) configured to transform the second liquid to the aerosol at a second temperature. In some embodiments, the first temperature is higher than the second temperature by at least 30° F. when the second temperature is maintained below 125° F. In some embodiments, the first temperature is higher than the second temperature by at least 40° F., at least 50° F., at least 60° F., at least 70° F., at least 80° F., at least 90° F., or by at least 100° F. when the second temperature is maintained below 120° F., 125° F., or 130° F.

In some embodiments, the aerosolization element includes an ultrasonic nebulizer, a jet nebulizer, a soft mist inhaler, or a mesh nebulizer.

In some embodiments, the nebulizer module is configured to combine the inhalant and the aerosol to be administered to the user as a combined aerosol.

In some embodiments, the nebulizer module is configured to administer the inhalant and the aerosol to the user as separate aerosols.

In some embodiments, the nebulizer is configured to administer the inhalant to the user via an oral inhalation and the aerosol to the user via intranasal inhalation.

In some embodiments, the first liquid includes a cannabinoid compound (e.g., THCA) and the second liquid includes a flavor compound.

In some embodiments, the dosage module includes a first flow controller (e.g., the flow controller 134-1) coupled with the first reservoir and a second flow controller (e.g., the flow controller 134-2) coupled with the second reservoir. The first flow controller is configured to control a flow of the first liquid from the first reservoir to the nebulizer module. The second flow controller is configured to control a flow of the second liquid from the second reservoir to the nebulizer module.

In some embodiments, the device further includes a controller module (e.g., controller 132) configured to receive instruction from a user device that is separate from the nebulizer device. The user device is in wireless communication with the nebulizer device. The instructions include a dosing scheme (e.g., as illustrated in the screenshot 300 in FIG. 3) including the ratio between the first dosage of the first liquid and the second dosage of the second liquid. The dosing schema is associated with the user of the nebulizer device.

In accordance with some embodiments, a method for administering aerosol compounds to a user with a nebulizer device is disclosed. The nebulizer device includes a mouthpiece, a first reservoir, a second reservoir, a nebulizer module, and a dosage module. The method includes receiving, with the nebulizer module coupled with the first reservoir and the second reservoir distinct from the first reservoir, a first dosage of the first liquid from the first reservoir, and a second dosage of a second liquid from the second reservoir. The method includes transforming, with the nebulizer module, the received first liquid into an inhalant and the received second liquid into an aerosol that are provided to the user through the mouthpiece. The method includes controlling independently, with the dosage module, delivery of the first liquid and the second liquid to the nebulizer module to set a ratio between the first dosage of the first liquid and the second dosage of the second liquid. The method thereby controls a composition of an aerosol cannabinoid mixture administered to the user. The aerosol cannabinoid mixture includes the inhalant and the aerosol.

In accordance with some embodiments, a controller module (e.g., controller 132) for administering aerosol cannabinoid mixtures to a user by a portable nebulizer device is disclosed. The controller includes a processor and a memory storing instructions which, when executed by the processor, cause the nebulizer device to perform the methods described herein.

In accordance with some embodiments, a system (e.g., the system 100 in FIG. 1) for providing aerosol compounds to a user includes a nebulizer device and a user device. The nebulizer device includes a mouthpiece (e.g., the mouthpiece 120), a first reservoir, and a second reservoir (e.g., the reservoirs 122-1 and 122-2). The second reservoir is separate from the first reservoir. The nebulizer device also includes a nebulizer module (e.g., the nebulizer module 124) fluidically coupled to the first reservoir and the second reservoir. The nebulizer module is configured to receive a first dosage of the first liquid from the first reservoir and a second dosage of a second liquid from the second reservoir. The nebulizer module is configured to transform the received first liquid into an inhalant and the received second liquid into an aerosol that are provided to the user through the mouthpiece. The nebulizer device also includes a dosage module (e.g., the dosage module 130) configured to independently control delivery of the first liquid and the second liquid to the nebulizer module to set a ratio between the first dosage of the first liquid and the second dosage of the second liquid. The dosage module thereby controls a composition of an aerosol cannabinoid mixture administered to the user. The aerosol cannabinoid mixture includes the inhalant and the aerosol.

The user device (e.g., the user device 110) is in communication with the nebulizer device. The user device includes a processor and a memory (e.g., the processor 605 and memory 610 of computing system 600 in FIG. 6) storing instructions which, when executed by the processor, cause the user device to receive a dosing schema from the user of the user device. The dosing schema (e.g., as shown in the screenshot 300 in FIG. 3) includes the ratio between the first dosage of the first liquid and the second dosage of the second liquid. The dosing schema is associated with the user of the nebulizer device. The instructions further cause the user device to provide instructions to the nebulizer device to administer the first dosage of the first liquid and the second dosage of the second liquid to the nebulizer module in accordance with the dosing schema.

In some embodiments, the dosing schema includes a type of compound (e.g., CBD 1, 2, 3, 4 in FIG. 3) for the first liquid and a type of compound for the second liquid (e.g., Flavor 1, 2, 3, 4). The dosing schema can include a set of dosing schemas over a period of time.

In some embodiments, the dosage module is configured to receive the dosing schema from the user device and obtain information regarding a compound cartridge inserted in the nebulizer device (e.g., a compound cartridge including the reservoirs 122-1 and 122-2 in FIG. 2A). The compound cartridge includes the first reservoir and the second reservoir. The dosage module is also configured to set the ratio between the first dosage of the first liquid and the second dosage of the second liquid based on the dosing schema and the information regarding the compound cartridge.

In some embodiments, the instructions further cause the system to display, on a display of the user device, a graphical user interface including information related to the dosing schema (e.g., the screenshot 300 in FIG. 3 displayed by the user device GUI 114 in FIG. 1).

In some embodiments, the instructions further cause the system to receive, by the user device, a user input for defining the dosing schema.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include, but are not limited to, physically mateable and/or physically interacting components and/or wirelessly interactable and/or wirelessly interacting components and/or logically interacting and/or logically interactable components.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A portable device for administering aerosol mixtures to a user, the portable device comprising:
- a mouthpiece including a first outlet;
- a nozzle including a second outlet;
- a first reservoir and a second reservoir separate from the first reservoir;
- a nebulizer module fluidically coupled to the first reservoir and the second reservoir, the nebulizer module configured to:
  - receive a first amount of a first liquid from the first reservoir and a second amount of a second liquid from the second reservoir,
  - transform the received first liquid into an inhalant and the received second liquid into an aerosol wherein the first liquid includes at least one cannabinoid compound and the second liquid includes at least one flavor compound,
  - use at least one sensor of the portable device to detect if the at least one flavor compound has volatized into at least one harmful chemical to control the aerosol being provided to the user to avoid lung irritation of the user,
  - output the inhalant and aerosol to the first outlet and second outlet as first and second parallel streams, respectively, wherein the second stream is expelled from the second outlet into an atmosphere around the user, and
- a dosage module configured to independently control delivery of the first liquid and the second liquid to the nebulizer module.

2. The portable device of claim 1, wherein the dosage module includes:
- a first flow controller coupled with the first reservoir and configured to control a flow of the first liquid from the first reservoir to the nebulizer module; and
- a second flow controller coupled with the second reservoir and configured to control a flow of the second liquid from the second reservoir to the nebulizer module.

3. The portable device of claim 1, wherein:
- the portable device is configured to be in communication with a wearable device worn by the user, wherein the wearable device is configured to track a health indication associated with the user, and
- the portable device is configured to receive an at least one health indication from the wearable device.

4. The portable device of claim 3, wherein the wearable device is a smartwatch or a smartband and the portable device is in communication with a user device that is a smartphone or a tablet computer.

5. The portable device of claim 3, wherein the at least one health indication includes a heart rate, and in response to the heart rate reaching above a threshold, automatically adjusting the amount of the first liquid including the cannabinoid compound.

6. The portable device of claim 3, wherein the at least one health indication includes a biometric indication, and in response to the biometric indication being above or below a threshold, automatically adjusting the amount of the first liquid including the cannabinoid compound.

7. A method for administering aerosol compounds to a user with a nebulizer device including a mouthpiece including a first outlet, a second outlet, a first reservoir, a second reservoir, a nebulizer module, and a dosage module, the method comprising:
- receiving, with the nebulizer module, a first amount of a first liquid from the first reservoir and a second amount of a second liquid from the second reservoir, wherein:
  - the second reservoir is separate from the first reservoir,
  - the nebulizer module is fluidically coupled to the first reservoir and the second reservoir; transforming, by the nebulizer module, the received first liquid into an inhalant and the received second liquid into an aerosol, wherein the first liquid includes at least one cannabinoid compound and the second liquid includes at least one flavor compound,
  - at least one sensor of the nebulizer device is configured to detect if the at least one flavor compound has volatized into at least one harmful chemical, the nebulizer module is configured control the aerosol being provided to the user based on the detection of the at least one harmful chemical to avoid lung irritation of the user,
  - the inhalant and aerosol are output to the first outlet and second outlet, respectively and in-parallel, wherein the at least one flavor compound is expelled from the second outlet into an atmosphere around the user, and
- independently controlling, by the dosage module, delivery of the first liquid and the second liquid to the nebulizer module.

8. The method of claim 7, further comprising:
- controlling, by a first flow controller coupled with the first reservoir, a flow of the first liquid from the first reservoir to the nebulizer module, and
- controlling, by a second flow controller coupled with the second reservoir, a flow of the second liquid from the second reservoir to the nebulizer module.

9. The method of claim 7, further comprising:
automatically adjusting, by a controller module, a set ratio between the first amount of the first liquid and the second amount of the second liquid in accordance with a user-specific dosing scheme, wherein the user-specific dosing scheme includes independently increasing or decreasing the first amount of the first liquid and/or the amount of the second liquid while the inhalant and the aerosol are independently output from the first outlet and second outlet.

10. The method of claim 9, wherein the user-specific dosing scheme is based on information regarding at least one compound cartridge inserted into the nebulizer device, wherein the at least one compound cartridge includes the first liquid and the second liquid.

11. The method of claim 9, further comprising:
automatically adjusting, by the controller module, the user-specific dosing scheme based on a time of a day or in response to at least one health indication associated with the user, and
the ratio between the first amount of the first liquid and the second amount of the second liquid is adjusted according to the adjusted user-specific dosing scheme.

12. The method of claim 11, wherein:
the nebulizer device is in communication with a wearable device,
the wearable device worn by the user is configured to track the health indication associated with the user, and
the method further comprises, receiving, by the nebulizer device, the at least one health indication from the wearable device.

13. A portable device for administering aerosol mixtures to a user, the device comprising:
a mouthpiece including a first outlet;
a nozzle including a second outlet;
a first reservoir and a second reservoir separate from the first reservoir;
a nebulizer module fluidically coupled to the first reservoir and the second reservoir, the nebulizer module configured to:
receive a first amount of a first liquid from the first reservoir and a second amount of a second liquid from the second reservoir, wherein the first liquid is comprised of one or more psychoactive substances, and the second liquid is comprised of at least one flavor compound,
transform the received first liquid into an inhalant and the received second liquid into an aerosol,
use at least one sensor of the portable device to detect if the at least one flavor compound has volatized into at least one harmful chemical to control the aerosol being provided to the user to avoid lung irritation of the user,
output the inhalant and aerosol to the first outlet and second outlet as first and second parallel streams, respectively, wherein the second stream is expelled from the second outlet into an atmosphere around the user without requiring direct inhalation of the second output stream by the user, and
a dosage module configured to independently control delivery of the first liquid and the second liquid to the nebulizer module.

* * * * *